United States Patent
Gross et al.

(10) Patent No.: US 7,614,998 B2
(45) Date of Patent: Nov. 10, 2009

(54) FULLY-IMPLANTABLE CARDIAC RECOVERY SYSTEM

(76) Inventors: Yossi Gross, 10 HaNotea Street, Moshav Mazor 73160 (IL); Ra'anan Gefen, P.O. Box 1224, Re'ut 71908 (IL)

(*) Notice: Subject to any disclaimer, the term of this patent is extended or adjusted under 35 U.S.C. 154(b) by 419 days.

(21) Appl. No.: 10/546,660

(22) PCT Filed: Feb. 24, 2004

(86) PCT No.: PCT/IL2004/000183

§ 371 (c)(1),
(2), (4) Date: Apr. 13, 2006

(87) PCT Pub. No.: WO2004/073484

PCT Pub. Date: Sep. 2, 2004

(65) Prior Publication Data

US 2006/0217588 A1 Sep. 28, 2006

Related U.S. Application Data

(60) Provisional application No. 60/449,495, filed on Feb. 24, 2003.

(51) Int. Cl.
*A61B 1/00* (2006.01)
(52) U.S. Cl. ........................................................ 600/17
(58) Field of Classification Search ............... 600/16–18
See application file for complete search history.

(56) References Cited

U.S. PATENT DOCUMENTS

| 3,585,983 A | 6/1971 | Kantrowitz et al. |
| 3,866,604 A | 2/1975 | Curless et al. |
| 4,240,409 A | 12/1980 | Robinson et al. |
| 4,245,622 A | 1/1981 | Hutchins, IV |
| 4,583,523 A | 4/1986 | Kleinke et al. |
| 4,630,597 A | 12/1986 | Kantrowitz et al. |
| 4,809,676 A | 3/1989 | Freeman |
| 4,938,766 A | 7/1990 | Jarvik |
| 5,130,141 A | 7/1992 | Law et al. |
| 5,346,476 A * | 9/1994 | Elson ........................ 604/135 |
| 5,466,221 A * | 11/1995 | Zadini et al. .................. 600/18 |

(Continued)

FOREIGN PATENT DOCUMENTS
EP 1078649 2/2001

(Continued)

OTHER PUBLICATIONS
U.S. Appl. No. 60/651,751, 2005.

(Continued)

*Primary Examiner*—Scott M Getzow
(74) *Attorney, Agent, or Firm*—Ladas and Parry LLP

(57) ABSTRACT

Apparatus (20) is provided including an inflatable bladder (40), adapted to be coupled to a blood vessel (22) of a subject (18) carrying oxygenated blood, such that an interior of the bladder (40) is in fluid communication with the blood. The apparatus also includes a piston (48) in mechanical communication with the bladder (40); a motor (60), adapted to synchronize contraction and expansion of the bladder (40) with a cardiac cycle of the subject (18) by applying a motor force to the piston (48); and a spring (54), adapted to apply a spring force to the piston (48).

30 Claims, 22 Drawing Sheets

U.S. PATENT DOCUMENTS

| | | | |
|---|---|---|---|
| 5,514,079 A | 5/1996 | Dillon et al. | |
| 5,554,103 A | 9/1996 | Zheng et al. | |
| 5,997,540 A | 12/1999 | Zheng et al. | |
| 6,030,336 A * | 2/2000 | Franchi | 600/18 |
| 6,057,689 A * | 5/2000 | Saadat | 324/557 |
| 6,100,242 A | 8/2000 | Hammond et al. | |
| 6,132,363 A | 10/2000 | Freed et al. | |
| 6,200,260 B1 | 3/2001 | Bolling et al. | |
| 6,223,648 B1 | 5/2001 | Erickson | |
| 6,297,220 B1 | 10/2001 | Leiden et al. | |
| 6,299,575 B1 | 10/2001 | Bolling | |
| 6,306,830 B1 | 10/2001 | Hammond et al. | |
| 6,376,971 B1 | 4/2002 | Pelrine et al. | |
| 6,387,037 B1 | 5/2002 | Bolling et al. | |
| 6,390,969 B1 | 5/2002 | Bolling et al. | |
| 6,406,422 B1 | 6/2002 | Landesberg | |
| 6,428,464 B1 | 8/2002 | Bolling et al. | |
| 6,450,942 B1 | 9/2002 | Lapanashvili et al. | |
| 6,468,200 B1 | 10/2002 | Fischi | |
| 6,511,413 B2 | 1/2003 | Landesberg | |
| 6,545,384 B1 | 4/2003 | Pelrine et al. | |
| 6,572,652 B2 | 6/2003 | Shaknovich | |
| 6,586,859 B2 | 7/2003 | Kornbluh et al. | |
| 6,673,043 B1 | 1/2004 | Landesberg | |
| 6,685,621 B2 | 2/2004 | Bolling et al. | |
| 6,808,484 B1 * | 10/2004 | Peters et al. | 600/18 |
| 2002/0103413 A1 * | 8/2002 | Bugge et al. | 600/16 |
| 2002/0151761 A1 | 10/2002 | Viole et al. | |
| 2002/0173693 A1 | 11/2002 | Landesberg | |
| 2002/0173735 A1 | 11/2002 | Lewis | |
| 2003/0045909 A1 | 3/2003 | Gross et al. | |
| 2003/0163020 A1 | 8/2003 | Fraizer | |

FOREIGN PATENT DOCUMENTS

| | | |
|---|---|---|
| WO | WO 02/24254 | 3/2002 |
| WO | WO 02/28470 | 4/2002 |
| WO | WO 03/099377 | 12/2003 |

OTHER PUBLICATIONS

U.S. Appl. No. 60/449,495, 2003.

* cited by examiner

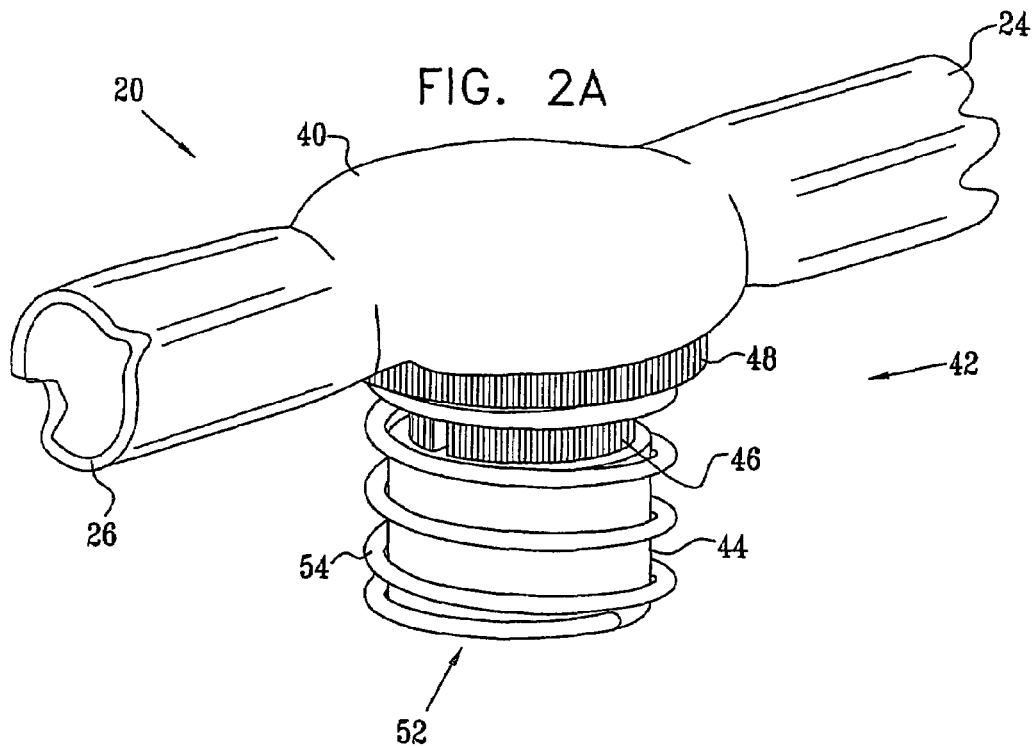
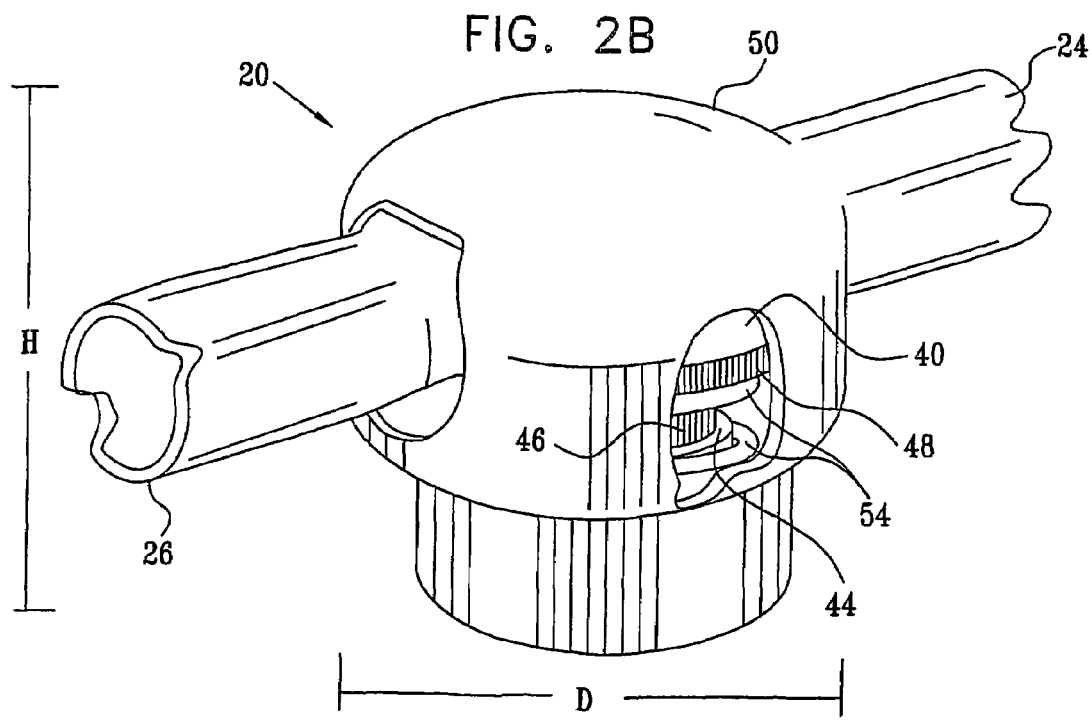

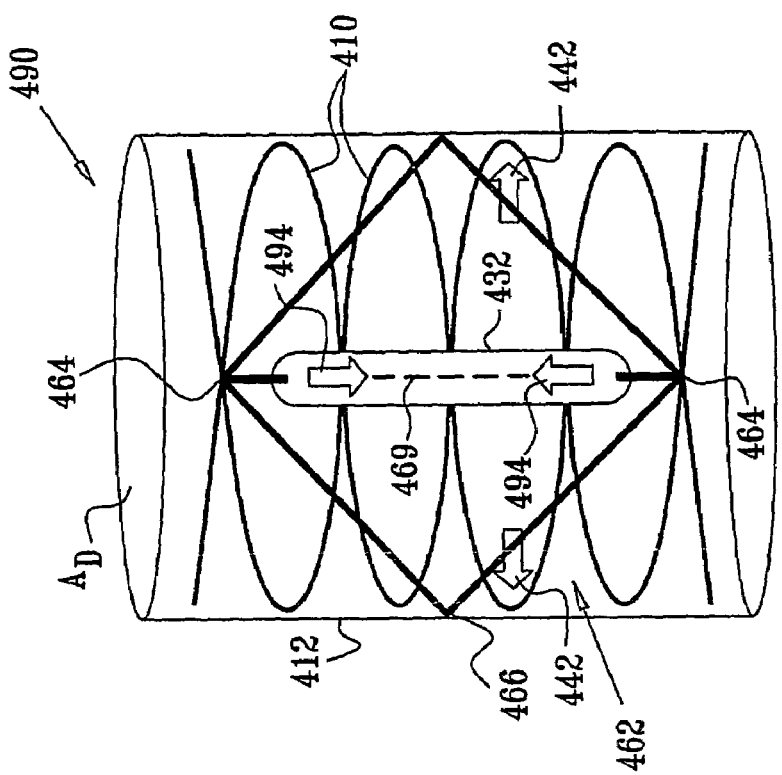
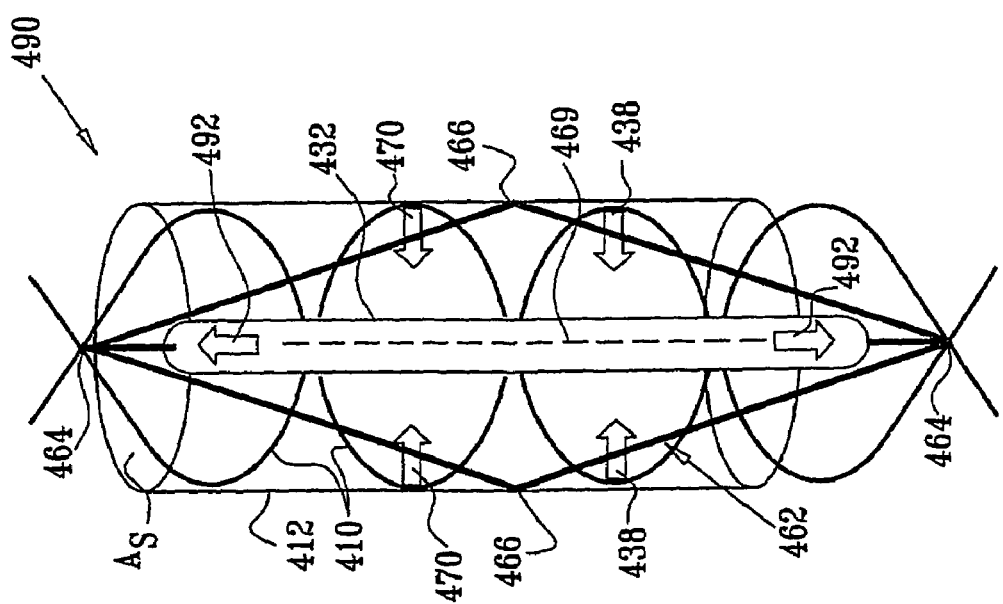

FULLY-IMPLANTABLE CARDIAC RECOVERY SYSTEM

CROSS-REFERENCES TO RELATED APPLICATIONS

This application claims the benefit of U.S. Provisional Application 60/449,495, filed Feb. 24, 2003, entitled, "Fully-implantable cardiac recovery system," which is assigned to the assignee of the present application and is incorporated herein by reference.

FIELD OF THE INVENTION

The present invention relates generally to implantable medical devices, and specifically to methods and apparatus for implantable devices for treating heart failure, hypertension, and other cardiovascular conditions.

BACKGROUND OF THE INVENTION

Heart failure is a chronic cardiac condition characterized by a deficiency in the ability of the heart to pump blood. Decreased cardiac output to the systemic circulation typically increases venous blood pressure, which often leads to blood backing up in the lungs. Low cardiac output also results in decreased blood perfusion to organs, such as the liver, kidney, brain, and heart itself. Over time, the effects of heart failure contribute to a worsening of the condition. Reduced blood supply to the heart causes less effective contraction of the heart. At the same time, higher venous blood pressure increases the heart preload. To compensate, the heart attempts to increase output by increasing muscle strength, which leads to myocardial hypertrophy (enlargement of the heart with thickening and stiffening of the heart wall). These conditions in turn lead to reduced cardiac output, resulting in a vicious cycle.

There are primarily two types of heart failure, systolic heart failure and diastolic heart failure. Systolic heart failure is characterized by a deficiency in systolic heart function, which causes insufficient expulsion of blood during systole. Diastolic heart failure is characterized by a deficiency in diastolic heart function, which causes insufficient ventricular filling during diastole.

Treatment for heart failure varies with the severity of the disease. Moderate heart failure is generally treated with lifestyle changes and medication, such as diuretics, digitalis, ACE inhibitors, and beta-blockers. Heart failure is also sometimes treated with cardiac resynchronization therapy (CRT) by implanting a biventricular pacemaker to synchronize the beating activity of both sides of the heart. CRT may be combined with implantable cardioverter-defibrillator (ICD) therapy. Severe heart failure may be treated with a heart transplant, a temporary artificial heart, or a ventricular assist device (VAD). A VAD is a blood pump designed to assist or replace the function of either one or both ventricles of the heart, on a short-term basis. VADs include right ventricular assist devices (RVAD), left ventricular assist devices (LVAD), and biventricular assist devices (BVAD). VADs may be either external or implantable.

An intra-aortic balloon pump (IABP) is sometimes used on a short-term basis for patients awaiting a heart transplant, or for patients recovering from open-heart surgery, also on a short-term basis. An IABP is a balloon that is generally placed in the aorta of a patient, and is inflated during diastole and deflated during systole, so as to reduce left ventricular preload and afterload. For example, U.S. Pat. No. 6,468,200 to Fischi, which is incorporated herein by reference, describes an IABP including a multiple-chamber balloon disposed at the distal portion of a catheter.

Counterpulsation is a technique for assisting the circulation by decreasing the afterload of the left ventricle and augmenting the diastolic pressure. Devices for achieving counterpulsation include intra-aortic balloons, pumping devices implantable in the chest, and external devices that apply a negative pressure to the lower extremities during cardiac systole. Counterpulsation devices are typically synchronized with a patient's cardiac cycle to apply pressure to blood vessels of the patient during diastole, and to remove the applied pressure immediately prior to systole, so as to increase stroke volume by decreasing afterload, to reduce heart workload, and to maintain or increase coronary perfusion. Counterpulsation techniques have been studied since the mid-1950s. Birtwell W C et al., in "The evolution of counterpulsation techniques," Med. Instrum. 10:217-223 (1976), which is incorporated herein by reference, review the history of various counterpulsation techniques. Clauss R H et al., in "Assisted Circulation: 1. The Arterial Counterpulsator," Journal of Thoracic and Cardiovascular Surgery 41:447 (1961), which is incorporated herein by reference, describe a pump placed on the arterial side of the circulation and used to alter the pressure of the left intraventricular aortic and arterial pulses. Unger F et al., in "The Windkesselventricle with guiding balloon as a new approach to assisted circulation," Med. Instrum. 10:256-259 (1976), which is incorporated herein by reference, describe the implantation of balloons in aortas of dogs and a method for pneumatically driving the balloons synchronously with electrocardiogram (ECG) measurements, so as to increase hemodynamic efficiency.

Externally-applied counterpulsation devices are described, for example, in U.S. Pat. Nos. 5,554,103 and 5,997,540 to Zheng et al., and U.S. Pat. No. 3,866,604 to Curless et al., all of which are incorporated herein by reference. U.S. Pat. No. 5,514,079 to Dillon, which is incorporated herein by reference, describes techniques for improving circulation by applying external positive regional pressure on an extremity synchronously with the patient's heartbeat. An adjustable timing cycle is initiated at the QRS complex of the arterial pulse cycle. US Patent Application Publication 2002/0173735 to Lewis, which is incorporated herein by reference, describes a medical device for non-invasive counterpulsation treatment of heart disease and circulatory disorders through external cardiac assistance. The device comprises cuffs which are affixed on a patient's lower body and extremities, and which constrict by electromechanical activation, thereby augmenting blood pressure for treatment purposes.

US Patent Application Publication 2002/0173693 to Landesberg, which is incorporated herein by reference, describes a system for assisting a failing ventricle, which utilizes a single blood displacement chamber and a single cannula. The cannula is inserted into the failing ventricle cavity and is connected to a blood displacement actuator. The device is described as producing blood displacement at a critical time for a critical duration and with blood flow time course such that it improves the systolic function of the heart, augments cardiac output, and increases the generated pressure. The device is also described as improving diastolic function by increasing the ventricle compliance and imposing rapid relaxation of the ventricle wall. The device is described as providing additional external work without deteriorating the mechanical function of the failing ventricle, moreover it is described as decreasing the energy consumption of the failing heart and improving coronary perfusion. Consequently, the device is described as improving the balance between the energy supply (coronary perfusion) to the ventricle wall and the mechanical demands, and to thereby allow recovery of the failing heart.

U.S. Pat. Nos. 6,673,043, 6,406,422, and 6,511,413, also to Landesberg, describe related techniques to those described in the above-cited US Patent Application Publication 2002/0173693. These patents are incorporated herein by reference, as well.

PCT Publication WO 02/24254A2 to Khaghani et al., which is incorporated herein by reference, describes a blood circulation assistance device for location around a blood conduit. The device comprises an inflatable bladder for compressing the blood conduit to provide counterpulsation, and a pump for contracting and expanding the bladder. The pump expands the bladder at diastole, as determined by monitoring the cardiac cycle. An outer cuff surrounds the bladder in order to provide an outer limiting extent to the movement of the bladder.

U.S. Pat. No. 4,938,766 to Jarvik, which is incorporated herein by reference, describes implantable prosthetic devices and methods of use for increasing blood flow by increasing arterial compliance and reducing the magnitude of the pressure pulsations in the arterial system, and to increase perfusion of specific organs in order to overcome the deleterious effects of cardiovascular disease.

U.S. Pat. No. 6,030,336 to Franchi, which is incorporated herein by reference, describes a pump comprising variable volume means inserted in an artery, in particular, the descending aorta, enabling the volume through which the blood flows in this location to be modified cyclically and in a controlled manner. The device comprises a deformable enclosure in fluid communication with the variable volume. The variable volume and a spring coil urge the deformable enclosure against an increase of volume resulting from a pressure increase in the variable volume, and in the corresponding enclosure, so as to produce additional elastance for the artery during the heart cycle. In addition, an electric motor can control the deformable enclosure to increase or decrease its volume, and can exert its force in addition to or in subtraction from the force of the spring coil during the systolic and diastolic phases of the heart cycle.

U.S. Pat. No. 6,450,942 and European Patent Application 1 078 649 A1 to Lapanashvili et al., which are incorporated herein by reference, describe a technique for reducing heart load by measuring heart rhythm, and producing pressure pulsations in the peripheral vascular system in synchronization with the heart rhythm in a counterpulsation mode, so as to reduce pulse rate and/or systolic pressure, and thereby heart load.

U.S. Pat. Nos. 6,200,260, 6,299,575, and 6,428,464 to Bolling; U.S. Pat. Nos. 6,387,037, 6,390,969, and 6,685,621 to Bolling et al.; and US Patent Application 2003/0088147 to Bolling et al., all of which are incorporated herein by reference, describe an extracardiac pumping system comprising a pump implanted subcutaneously at a patient's groin. The pump draws blood from the patient's femoral artery and discharges blood to a peripheral artery that stems from the patient's aortic arch. The pump may be operated continuously or in a pulsatile fashion, synchronous with the patient's heart, thereby potentially reducing the pumping load on the heart.

U.S. Pat. No. 6,132,363 to Freed et al., which is incorporated herein by reference, describes a left ventricular-assist device comprising an inflatable bladder sutured into the wall of the descending thoracic aorta, a percutaneous access device (PAD) implanted in a hypogastric region of the patient and in fluid communication with the bladder, and a drive unit connectible through the PAD for selectively inflating and deflating the bladder.

US Patent Application Publication 2002/0151761 to Viole et al., which is incorporated herein by reference, describes an intravascular extracardiac system, comprising a pump with inflow and outflow conduits that are implanted intravascularly through a non-primary vessel, and positioned within the patient's vasculature. The pump is configured to be operated continuously or in a pulsatile fashion, synchronous with the patient's heart, thereby potentially reducing the afterload of the heart.

U.S. Pat. No. 3,585,983 to Kantrowitz et al. which is incorporated herein by reference, describes an intra-arterial cardiac-assist device having a balloon which is inflated periodically for diastolic augmentation. U.S. Pat. No. 4,630,597 to Kantrowitz et al., which is incorporated herein by reference, describes a dynamic aortic patch that is permanently surgically implanted in the wall of the aorta to augment the pumping action of the heart. The patch comprises an elongate semi-rigid shell member having a concave inner surface and a flexible membrane integrally bonded to the outer surface of the shell to define an inflatable and deflatable chamber between the concave inner surface and the membrane.

U.S. Pat. No. 4,240,409 to Robinson et al., which is incorporated herein by reference, describes a device for mechanically assisting circulation of blood in a patient for periods of up to two weeks until the patient's heart strengthens sufficiently to take over the full workload. The circulatory assist device includes a valveless pump with a flexible bladder, a pneumatic driver for applying pressure pulses to the bladder, and a single flexible conduit for conveying blood between the patient and the pump. In use, the pump and driver are mounted external to the patient's body and the flexible conduit is connected to the pump and in end-to-side relationship with a major blood vessel on that side of the heart, either right or left, which is in need of support.

U.S. Pat. No. 6,406,422 to Landesberg, which is incorporated herein by reference, describes a ventricular-assist system that utilizes an intraventricular device with a limited volume. The device is expanded at a critical time, for a critical duration, and with a volume change course such that it assists the pumping action of the heart without inducing stretching of the ventricular wall.

U.S. Pat. No. 4,809,676 to Freeman, which is incorporated herein by reference, describes an implantable heart assist device that includes a member to be surgically positioned about the aorta, and a series of electromagnetic segments connected electrically to a source of electricity implanted within or without the body. The electromagnetic segments are C-shaped, and are arranged in pairs. The segments of each pair are positioned opposite to one another in confronting relation surrounding the aorta, and the electrical source is used to energize the segments of each pair to cause the segments to be moved forceably toward one another electromagnetically. Thus, the aorta is squeezed between each pair of segments.

U.S. Pat. No. 4,583,523 to Kleinke et al., which is incorporated herein by reference, describes an implantable heart assist device that includes an elongated assembly extending transversely between the ribs of a person from the rib cage to the aorta of the heart to be assisted. The elongated assembly includes an aorta compressing device at the front end thereof for engaging the aorta externally thereof. A mounting device at the rear end of the elongated assembly supports the device from the ribs of the person, and a motive device actuates and deactivates the compressing means alternatingly to help pump blood through the aorta.

U.S. Pat. No. 4,245,622 to Hutchins, IV, which is incorporated herein by reference, describes an inflatable/deflatable device for use in a body-implantable heart-assist pump. The device includes an inflatable/deflatable central portion, and a noninflatable, generally planar marginal portion joined thereto. In a preferred construction, the device is formed by the marginal joinder of a pair of flexible fluid-impervious sheets, wherein the central portion has opposite sides, and the marginal portion includes stretches distributed along these sides. The two flexible sheets may have different flexibilities, permitting the device to be inflated preferentially in a desired direction, and different curvatures, permitting the device to conform to adjoining surfaces in the heart-assist pump.

US Patent Application 2003/0163020 to Frazier, which is incorporated herein by reference, describes a heart assist system that includes an axial-flow blood pump capable of being implanted in the descending thoracic aorta; a pressure-feedback controller connected to the pump, for controlling the pump, the controller capable of being implanted in the body; and a rechargeable battery pack connected to the pump and to the controller, for providing power to the pump, the battery pack capable of being implanted in the body. A method for assisting a failing heart comprises (a) in response to when a measured dP/dT signal increases during systole, signaling an implanted aortic blood pump to go into a systolic mode and pump blood at a first flow rate; and (b) in response to when the dP/dT signal peaks in the negative region, signaling the pump to go into a diastolic mode and pump blood at a second flow rate.

US Patent Application 2003/0045909 to Gross et al., which is incorporated herein by reference, describes apparatus for treating heart conditions, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

PCT Publication WO 03/099377 to Ayal et al., which is incorporated herein by reference, describes apparatus for treating a subject, including an electrode device, adapted to be coupled to a vagus nerve of the subject, and a heart rate sensor, configured to detect a heart rate of the subject, and to generate a heart rate signal responsive thereto. The apparatus also includes a control unit, adapted to receive the heart rate signal, and, responsive to determining that the heart rate is greater than a threshold value, which threshold value is greater than a normal heart rate, drive the electrode device to apply a current to the vagus nerve, and configure the current so as to reduce the heart rate of the subject.

"Artificial muscles" are linear actuators that utilize polymers that undergo reversible length changes responsively to electrical or chemical stimuli. Artificial muscles thus convert electrical or chemical energy to mechanical energy. Artificial muscles are well known in the art, and are described for example, in the following patents and publication, all of which are incorporated herein by reference:

U.S. Pat. Nos. 6,545,384 and 6,376,971 to Pelrine et al.;
U.S. Pat. No. 6,223,648 to Erickson;
U.S. Pat. No. 6,586,859 to Kornbluh et al.; and Brock D L, "Review of artificial muscle based on contractile polymers," MIT Artificial Intelligence Laboratory, A.I. Memo No. 1330 (November 1991)

Cell therapy is an approach for repairing and augmenting diseased muscles, such as cardiac muscles. Myogenic cells are cultured and introduced into damaged muscle tissue, such as heart or striated muscle. The myogenic cells fuse with pre-existing muscle cells, transferring into the pre-existing muscle cells the normal genome in their nuclei in order to genetically repair the damaged muscle cells. U.S. Pat. No. 5,130,141 to Law et al., which is incorporated herein by reference, describes compositions for and methods of treating muscle weakness and degeneration. Such compositions include myogenic cells which are administered by the described methods to one or more affected muscles. PCT Publication WO 02/28470 to Law, which is incorporated herein by reference, describes catheters and methods for their use that provide automated delivery of cells to structures in the body such as degenerative or weak muscle.

Gene therapy is the delivery of foreign genes into cells for therapeutic purposes. U.S. Pat. No. 6,297,220 to Leiden et al., which is incorporated herein by reference, describes the use of adenovirus-mediated gene transfer to regulate function in cardiac and vascular smooth muscle cells. A recombinant adenovirus comprising a DNA sequence that codes for a gene product is delivered to a cardiac or vascular smooth muscle cell and the cell is maintained until that gene product is expressed. U.S. Pat. No. 6,100,242 to Hammond et al., which is incorporated herein by reference, describes the use of the transgene-inserted replication-deficit adenovirus vector in in vivo gene therapy for peripheral vascular disease and heart disease, including myocardial ischemia, by a single intrafemoral artery or intracoronary injection directly conducted deeply in the lumen of the one or both femoral or coronary arteries. U.S. Pat. No. 6,306,830 to Hammond et al., which is incorporated herein by reference, describes methods and compositions for enhancing cardiac function by inserting transgenes that increase beta-adrenergic responsiveness within the myocardium. These techniques are described as being useful for the treatment of heart disease, especially congestive heart failure.

SUMMARY OF THE INVENTION

In some embodiments of the present invention, an extra-cardiac fully-implantable cardiac recovery device comprises an inflatable bladder coupled to the descending aorta, e.g., the descending thoracic aorta, or a peripheral artery of a subject, such as an iliac artery or a left subclavian artery. The device, operating in a counterpulsation mode, regulates blood pressure in synchronization with the cardiac cycle of the subject by (a) accepting blood into the bladder immediately prior to and during systole, thereby reducing systemic blood pressure, and (b) ejecting the blood from the bladder during diastole, thereby increasing systemic blood pressure. The reduction in blood pressure prior to systole generally increases cardiac stroke volume by decreasing afterload, and reduces heart workload. The increased diastolic blood pressure generally increases coronary perfusion and lowers venous blood pressure, thereby reducing heart preload. Longer-term usage of the device generally improves heart contractility, reversing the vicious cycle that characterizes heart failure. The device is typically configured to operate as a heart assist device and/or a blood pressure regulation device, and is useful for treating subjects suffering from cardiovascular conditions such as heart failure, hypertension, angina, and/or ischemia. The device is typically suitable for long-term implantation and usage, including when the subject is active.

In some embodiments of the present invention, the cardiac recovery device comprises a regulation unit, adapted to regulate and synchronize the contraction and expansion of the bladder with the cardiac cycle. The regulation unit typically comprises a motor, such as a linear motor, or a compliance-regulation spring. For some applications, the regulation unit comprises both a motor and a spring, in which case the spring typically supports the action of the motor, thereby reducing the energy consumption of the motor. The device typically further comprises a piston, which is driven against the bladder by the motor and/or the spring, and a fixed case adapted to: (a) limit the expansion of the bladder in a direction opposite that of the regulation unit, and (b) cause the expansion of the bladder, which is induced by the high pressure during systole, to perform work on the spring (e.g., compress or extend the spring). For some applications, the piston is driven by hydraulic pressure instead of or in addition to the motor. In some embodiments of the present invention, the bladder comprises a flexible, non-elastic material. In other embodiments, including embodiments in which the device does not comprise a regulation unit, the bladder comprises an elastic material.

In some embodiments of the present invention, the cardiac recovery device is adapted to be coupled to a pulmonary vein of the subject. In these embodiments, the device further comprises a unidirectional valve, configured to substantially prevent backflow of blood from the pulmonary vein to the lungs. The device thus treats diastolic heart failure by increasing the flow of blood from one or both of the lungs to a left atrium of the subject.

In some embodiments of the present invention, the bladder comprises an inner layer and an outer layer, which define a chamber therebetween. The chamber comprises a substantially non-conductive biocompatible fluid, such as silicone oil. The chamber also comprises two or more electrodes, which are coupled to current-sensing means for sensing current flow between the electrodes. So long as both the inner and outer layers remain completely intact, the electrodes are electrically isolated from one another by the substantially non-conductive fluid. However, if either of the layers is breached, electrically conductive biological fluid enters the chamber, causing the electrodes to come into electrical contact with one another. The current-sensing means detects the electrical contact between the electrodes. Upon detection of such electrical contact, which is indicative of a leak in either of the layers, the device typically performs at least one responsive action, such as notifying the subject of the leak, and/or disabling the regulation unit.

In some embodiments of the present invention, a counterpulsation system comprises one or more springs, which are adapted to be inserted into an artery of a subject, such as a descending aorta. Typically, each of the springs is planar, i.e., flat rather than helical, and has a generally sinusoidal shape. For applications comprising more than one spring, the plurality of springs are arranged in substantially a single plane. The counterpulsation system causes the artery to have a cross-sectional area during diastole that is less than the cross-sectional area would be during diastole without use of the counterpulsation system. For example, the counterpulsation system may cause the artery to have a cross-sectional shape during diastole that generally resembles an ellipse. Use of the counterpulsation system thus typically increases diastolic blood pressure and decreases systolic blood pressure, thereby providing counterpulsation treatment to the circulation of the subject.

In the context of the present patent application and in the claims, the words "ellipse," "elliptical," and the like are to be understood to refer to a generally round shape having a characteristic major axis and minor axis, a ratio of lengths of the major axis to the minor axis being at least about 1.5:1.

For some applications, the ratio of lengths of the major axis to the minor axis is between about 1.5:1 and about 2:1. For other applications, the ratio of lengths of the major axis to the minor axis is between about 2:1 and 3:1.

In an embodiment, a neutral position of the one or more springs is approximately the shape that they attain by the end of diastole. Thus, they perform mechanical work on the artery during diastole as they move towards their neutral positions. During systole, the higher pressure in the artery forces the artery into a generally-circular cross-section, whereby the one or more springs are contracted laterally (and, correspondingly, shortened along their length). In this manner, energy is stored in the springs during systole. The energy is returned to the blood flow during diastole in the form of higher diastolic blood pressure.

In some embodiments of the present invention, the counterpulsation system additionally comprises a motor, typically coupled to the one or more springs at two points, each in a vicinity of an end of the springs. Immediately prior to systole, the motor applies longitudinal force towards the ends of the springs, which causes the springs to contract laterally, causing the cross-sectional area of the artery to increase, thereby decreasing systolic pressure and afterload. Alternatively, the motor applies the force towards the ends of the springs during systole, such as early in systole, rather than immediately prior to systole. During diastole, typically near the beginning of diastole, the motor applies longitudinal force towards the longitudinal center of the springs, which causes the springs to expand laterally, causing the cross-sectional area of the artery to decrease. Alternatively, the motor applies force immediately prior to or during systole only, or during diastole only.

In some embodiments of the present invention, the counterpulsation system comprises a frame: The motor is coupled to ends of the frame, such that the frame transforms longitudinal force applied by the motor into lateral movement of central side areas of the frame, which are in mechanical communication with the wall of the artery. (Alternatively, the motor itself is positioned so as to generate lateral movement of the frame directly, without the frame translating longitudinal force into lateral movement.) During systole, the motor applies longitudinal force towards the ends of the frame, which longitudinally stretches the frame. As a result, the central side areas of the frame move towards a longitudinal axis of the artery, causing the cross-sectional area of the artery to increase, as the artery's cross-sectional shape goes from elliptical to generally circular. During diastole, the motor applies longitudinal force towards the center of the frame, longitudinally compressing the frame. As a result, the central side areas of the frame move away from the longitudinal axis of the artery, causing the cross-sectional area of the artery to decrease. In some embodiments of the present invention utilizing the frame, the counterpulsation system comprises the motor, the one or more springs, and the frame, while in other embodiments the counterpulsation system comprises only the motor and the frame.

Treatment using the cardiac recovery device typically provides short- and long-term benefits to the subject. In the short-term, such treatment generally improves cardiac output and circulation, resulting in improved functioning of the subject, generally including the ability to be more active, and relief from symptoms of the condition being treated. Longer-term, lower cardiac load and increased coronary perfusion often reverses, arrests or slows the progression of the condition. Treatment may also improve the health of other organs damaged by heart failure. For some applications, the device is used to reduce cardiac load in subjects with heart failure risk factors such as hypertension, thereby preventing the development of heart failure and/or reducing cardiac stress. By reducing heart stress, the device generally facilitates the natural healing of the heart. Additionally, use of the device may facilitate cell therapy or gene therapy, because lower heart stress is generally a requirement for these therapies.

There is therefore provided, in accordance with an embodiment of the present invention, apparatus including:

an inflatable bladder, adapted to be coupled to a blood vessel of a subject carrying oxygenated blood, such that an interior of the bladder is in fluid communication with the blood;

a piston in mechanical communication with the bladder;

a motor, adapted to synchronize contraction and expansion of the bladder with a cardiac cycle of the subject by applying a motor force to the piston; and a spring, adapted to apply a spring force to the piston.

For some applications, the bladder is shaped so as to define an inflow opening and an outflow opening, and the bladder is adapted to be coupled to the blood vessel by coupling the inflow opening to a first site of the blood vessel, and the outflow opening to a second site of the blood vessel, such that the first site and second site are in fluid communication with one another only via the bladder.

For some applications, the blood vessel is selected from the list consisting of: a descending thoracic aorta of the subject, an iliac artery of the subject, a descending aorta of the subject, an ascending aorta of the subject, a femoral artery of the subject, and a peripheral artery of the subject, and the bladder is adapted to be implanted in the selected blood vessel. Alternatively, the blood vessel includes a pulmonary vein of the subject, and the bladder is adapted to be implanted in the pulmonary vein.

For some applications, the apparatus includes a case, adapted to prevent the bladder from expanding in a certain direction beyond a predetermined extent.

In an embodiment, the apparatus includes a locking mechanism, adapted to lock the piston in place for a portion of the cardiac cycle.

For some applications, the bladder includes a first conduit and a second conduit, and a common conduit, coupled to the first conduit and the second conduit, and adapted to be coupled to the blood vessel by anastomosis through a single opening in a wall of the blood vessel.

For some applications, the bladder holds between about 10 and about 100 ml of blood when in a fully expanded position.

For some applications, the bladder holds a volume when in a contracted position that is between about 10% and about 50% of a volume the bladder holds when in a fully expanded position. Alternatively, the bladder holds a volume when in a contracted position that is between about 50% and about 80% of a volume the bladder holds when in a fully expanded position. Further alternatively, the bladder holds a volume when in a contracted position that is less than about 10% of a volume the bladder holds when in a fully expanded position.

In an embodiment, the apparatus is configured such that during the contraction of the bladder, an apparatus-induced blood-containing volume of the blood vessel and the bladder in a vicinity of the apparatus is greater than or equal to an apparatus-absent blood-containing volume of the blood vessel in the vicinity in the absence of the apparatus.

In an embodiment, the apparatus is configured such that throughout the cardiac cycle, an apparatus-induced blood-containing volume of the blood vessel and the bladder in a vicinity of the apparatus is greater than or equal to an apparatus-absent blood-containing volume of the blood vessel in the vicinity in the absence of the apparatus.

For some applications, the bladder is shaped so as to define a single anastomosis site, and is adapted to be coupled to the blood vessel by anastomosis through a single opening in a wall of the blood vessel.

For some applications, the motor includes a linear motor. Alternatively, the motor includes an artificial muscle.

In an embodiment, the spring is configured to reduce an energy consumption of the motor by at least about 80% compared to the energy consumption in the absence of the spring.

In an embodiment, the apparatus is configured such that, in the event of a failure of the motor, the apparatus provides passive counterpulsation treatment to the subject.

For some applications, the bladder is shaped so as to define a first opening and a second opening, and the bladder is adapted to be coupled to the blood vessel by coupling the first opening to a first site of the blood vessel, and the second opening to a second site of the blood vessel, such that the first site and the second site are in fluid communication with one another via the blood vessel and via the bladder. For some applications, the bladder includes a first conduit and a second conduit, coupled to the first opening and the second opening, respectively, and the first conduit includes a constriction element, adapted to cause asymmetric blood flow through the bladder. For some applications, the constriction element includes a valve.

In an embodiment, the apparatus is configured such that upon the expansion of the bladder, an apparatus-induced blood-containing volume of the blood vessel and the bladder in a vicinity of the apparatus is greater than an apparatus-absent blood-containing volume of the blood vessel in the vicinity in the absence of the apparatus. For some applications, the apparatus is configured such that upon the expansion of the bladder, the apparatus-induced blood-containing volume is at least 10 ml greater than the apparatus-absent blood-containing volume. For some applications, the apparatus is configured such that upon the expansion of the bladder, the apparatus-induced blood-containing volume is at least 40 ml greater than the apparatus-absent blood-containing volume.

In an embodiment, the apparatus includes a sensor, adapted to sense a physiological parameter of the subject and to generate a sensor signal responsive thereto, and the motor is adapted to synchronize the contraction and the expansion of the bladder responsive to the sensor signal. For some applications, the motor is adapted to synchronize the contraction and expansion of the bladder according to a duty cycle. For some applications, the physiological parameter includes a blood pressure of the subject, and the sensor is adapted to sense the blood pressure and to generate the sensor signal responsive thereto.

For some applications, the physiological parameter includes an electrocardiographic parameter of the subject, and the sensor is adapted to sense the electrocardiographic parameter and to generate the sensor signal responsive thereto. For some applications, the motor is adapted to expand the bladder immediately prior to or during systole. Alternatively, the motor is adapted to contract the bladder at a point in time during or soon after a T-wave of the ECG.

There is further provided, in accordance with an embodiment of the present invention, apparatus including a counterpulsation device, which includes:

a motor, adapted to apply force to oxygenated blood of a subject during diastole;

a spring, adapted to store energy received from the oxygenated blood during systole, and to return the stored energy to the oxygenated blood during diastole; and an anastomosis site on a surface of the device, wherein the device is adapted to be implanted by anastomosis in communication with a blood vessel of a subject carrying oxygenated blood.

There is also provided, in accordance with an embodiment of the present invention, apparatus including a counterpulsation device, which includes:

a motor, adapted to apply force to oxygenated blood of a subject;

a control unit, adapted to determine an occurrence of diastole by detecting blood pressure applied to the motor, and to drive the motor to apply the force during diastole responsive to the determination; and a spring, adapted to store energy received from the blood during systole, and to return the stored energy to the blood during diastole.

For some applications, the control unit is adapted to determine the occurrence of diastole by detecting the blood pressure applied to the motor during systole. For some applications, the control unit is adapted to detect the blood pressure applied to the motor by detecting motion of the motor.

For some applications, the motor includes a piston, the piston adapted to apply, to the blood, the force generated by the motor, and the control unit is adapted to detect the blood pressure applied to the motor by detecting the blood pressure applied to the piston. For some applications, the control unit is adapted to detect the blood pressure applied to the piston by detecting motion of the piston.

There is additionally provided, in accordance with an embodiment of the present invention, apparatus including a counterpulsation device, which includes:

a spring, adapted to store energy received from oxygenated blood of the subject during systole, and to return the stored energy to the blood during diastole;

a motor, adapted to apply force to the blood; and a control unit, adapted to determine an occurrence of diastole by detecting blood pressure applied to the spring, and to drive the motor to apply the force during diastole responsive to the determination.

For some applications, the control unit is adapted to determine the occurrence of diastole by detecting the blood pressure applied to the spring during systole. For some applications, the control unit is adapted to detect the blood pressure applied to the spring by detecting a length of the spring.

There is yet additionally provided, in accordance with an embodiment of the present invention, apparatus including:

an inflatable bladder, including:

an inner layer and an outer layer, which define a chamber therebetween, the inner layer defining an interior of the bladder;

a biocompatible substantially non-conductive fluid, contained within the chamber;

two or more electrodes, in contact with the substantially non-conductive fluid; and a current sensing unit, coupled to the electrodes and adapted to sense current flow between at least two of the electrodes, wherein the bladder is adapted to be implanted in a subject such that the interior of the bladder is in fluid communication with blood of a blood vessel of the subject.

For some applications, at least one of the electrodes includes a wire having a length of at least 10 cm. Alternatively or additionally, at least one of the electrodes includes a conductive coating applied to a surface selected from: the inner layer and the outer layer.

For some applications, the substantially non-conductive fluid includes silicone oil.

For some applications, the apparatus includes a control unit, adapted to receive, from the current sensing unit, a signal indicative of a level of the sensed current flow, and to generate a notification signal when the level of the current flow crosses a threshold value.

For some applications, the current sensing unit includes a voltage source, adapted to apply a known small voltage between the electrodes, and a current sensor, adapted to detect a current that flows in response to the applied voltage.

There is still additionally provided, in accordance with an embodiment of the present invention, apparatus including:

an inflatable bladder, including:

an inner layer and an outer layer, which define a chamber therebetween, the inner layer defining an interior of the bladder;

a biocompatible substantially non-conductive fluid, contained within the chamber;

at least one electrode, in contact with the substantially non-conductive fluid; and a current sensing unit, including a first terminal and a second terminal, the first terminal electrically coupled to the electrode, and the second terminal in contact with extracellular fluid and the current sensing unit, wherein the bladder is adapted to be implanted in a subject such that the interior of the bladder is in fluid communication with blood of a blood vessel of the subject.

For some applications, the substantially non-conductive fluid includes silicone oil.

For some applications, the apparatus includes a control unit, adapted to receive, from the current sensing unit, a signal indicative of a level of the sensed current flow, and to generate a notification signal when the level of the current flow crosses a threshold value.

For some applications, the current sensing unit includes a voltage source, adapted to apply a known small voltage between the first and second terminals, and a current sensor, adapted to detect a current that flows in response to the applied voltage.

There is still further provided, in accordance with an embodiment of the present invention, apparatus for applying counterpulsation treatment to a subject, the apparatus including:

one or more springs, adapted to be inserted into a blood vessel of the subject carrying oxygenated blood, the springs configured to cause the blood vessel to assume an elliptical cross-sectional shape during at least a portion of diastole; and one or more protective elements, adapted to provide a protective interface between the springs and a wall of the blood vessel.

For some applications, the one or more springs include exactly one spring.

For some applications, the blood vessel includes an aorta of the subject, and the one or more springs have a size appropriate for insertion into the aorta. Alternatively, the blood vessel includes a peripheral artery of the subject, and the one or more springs have a size appropriate for insertion in the peripheral artery.

For some applications, the one or more springs are configured to cause a ratio of a major axis of the blood vessel when assuming the elliptical cross-sectional shape to a end-diastolic diameter of the blood vessel when not assuming the elliptical cross-sectional shape to be between about 1.1 and about 1.4. Alternatively or additionally, the one or more springs are configured to cause a ratio of a major axis of the blood vessel to a minor axis of the blood vessel when assuming the elliptical cross-sectional shape to be between about 1.5:1 and about 3:1.

For some applications, the one or more springs include a plurality of springs, and the plurality of springs have planar shapes and are arranged substantially in a single plane.

For some applications, the one or more springs include a plurality of springs, and the springs are connected to one another at at least a portion of points at which they intersect.

For some applications, the apparatus includes a frame, adapted to be inserted into the blood vessel, and to be positioned such that two or more portions of the frame are in mechanical communication with the blood vessel; and a motor, coupled to the frame and to the one or more springs, and adapted to apply, during at least a portion of diastole, a diastolic force to the frame that causes the portions of the frame to cause the blood vessel to assume the elliptical cross-sectional shape.

For some applications, at least one of the protective elements has a length between about 5 and about 30 cm.

For some applications, the apparatus is adapted for insertion into the blood vessel by catheterization.

For some applications, the one or more springs are configured to cause a ratio of a cross-sectional area of the blood vessel during the at least a portion of diastole to a cross-sectional area of the blood vessel during at least a portion of systole to be between about 0.2 and about 0.9. For some applications, the one or more springs are configured to cause the ratio to be between about 0.4 and about 0.7.

In an embodiment, the one or more springs are adapted to be positioned in the blood vessel perpendicular to a longitudinal axis of the blood vessel. For some applications, the one or more springs are configured to elongate during diastole, and to shorten during systole.

In an embodiment, the one or more springs are adapted to be positioned in the blood vessel parallel to a longitudinal axis of the blood vessel. For some applications, the one or more springs are configured to elongate during systole, and to shorten during diastole. For some applications, at least one of the protective elements is shaped so as to define a groove, configured such that the springs slide longitudinally in the groove.

In an embodiment, at least one of the springs has a planar shape. For some applications, the at least one of the springs has a generally sinusoidal shape.

In an embodiment, the apparatus includes a motor, coupled to the one or more springs, and adapted to apply force to the one or more springs. For some applications, the motor is adapted to elongate the one or more springs immediately prior to or during systole, and to shorten the one or more springs during diastole. Alternatively, the motor is adapted to elongate the one or more springs during diastole, and to shorten the one or more springs immediately prior to or during systole.

There is also provided, in accordance with an embodiment of the present invention, apparatus for applying counterpulsation treatment to a subject, the apparatus including:

one or more springs, adapted to be inserted into a blood vessel of the subject carrying oxygenated blood, the springs configured to cause the blood vessel to assume, during at least a portion of diastole, a spring-induced cross-sectional area that is less than a spring-absent cross-sectional area of the blood vessel in the absence of the springs during the portion of diastole; and one or more protective elements, adapted to provide a protective interface between the springs and a wall of the blood vessel.

There is further provided, in accordance with an embodiment of the present invention, apparatus for applying counterpulsation treatment to a subject, the apparatus including:

a frame, adapted to be inserted into a blood vessel of the subject carrying oxygenated blood, and to be positioned such that at least two portions of the frame are in mechanical communication with the blood vessel; and a motor, coupled to the frame, and adapted to apply, during at least a portion of diastole, a diastolic force to the frame that causes the portions of the frame to cause the blood vessel to assume an elliptical cross-sectional shape during the at least a portion of diastole.

For some applications, the motor is adapted to apply, during at least a portion of a period consisting of systole and immediately prior to systole, a systolic force to the frame.

For some applications, the blood vessel includes an aorta of the subject, and the frame has a size appropriate for insertion into the aorta. Alternatively, the blood vessel includes a peripheral artery of the subject, and the frame has a size appropriate for insertion into the peripheral artery.

In an embodiment, the motor is adapted to apply the diastolic force to the frame in a direction perpendicular to a longitudinal axis of the blood vessel.

In an embodiment, the motor is adapted to apply the diastolic force to the frame in a direction parallel to a longitudinal axis of the blood vessel, and the frame is configured to translate the diastolic force into force directed, at least in part, perpendicularly to the longitudinal axis.

For some applications, the frame includes one or more protective elements, adapted to provide a protective interface between the portions and a wall of the blood vessel.

For some applications, the motor includes a linear motor. Alternatively, the motor includes an artificial muscle.

For some applications, the apparatus includes a plurality of frames.

In an embodiment, the apparatus is configured such that, in the event of a failure of the motor, the apparatus allows the blood to flow in the blood vessel substantially without harmful restriction.

For some applications, the apparatus is adapted for insertion into the blood vessel by catheterization.

For some applications, the frame is configured to cause a ratio of a characteristic diastolic cross-sectional area to a characteristic systolic cross-sectional area to be between about 0.2 and about 0.9. For some applications, the frame is configured to cause the ratio to be between about 0.4 and about 0.7.

In an embodiment, the frame includes at least one spring. For some applications, the spring is oriented parallel to a longitudinal axis of the blood vessel. For some applications, the spring is oriented perpendicular to a longitudinal axis of the blood vessel. For some applications, the spring is configured to reduce an energy consumption of the motor by at least about 80% compared to the energy consumption in the absence of the spring.

In an embodiment, the frame includes four substantially rigid elongated members, arranged in a shape of a diamond, such that the members define four articulating joints therebetween. For some applications, the frame includes a spring, coupled to two of the joints located at opposite corners of the diamond.

There is still further provided, in accordance with an embodiment of the present invention, apparatus for applying counterpulsation treatment to a subject, the apparatus including:

a frame, adapted to be inserted into a blood vessel of the subject carrying oxygenated blood, and to be positioned such that at least a portion of the frame is in mechanical communication with the blood vessel; and a motor, coupled to the frame, and adapted to apply a force to the frame that causes the portion of the frame to cause the blood vessel to assume, during at least a portion of diastole, a frame-induced cross-sectional area that is less than a frame-absent cross-sectional area of the blood vessel in the absence of the frame during the at least a portion of diastole.

There is additionally provided, in accordance with an embodiment of the present invention, apparatus for applying counterpulsation treatment to a subject, the apparatus including a motor, adapted to be inserted into a blood vessel of the subject carrying oxygenated blood, the motor adapted to apply, during at least a portion of diastole, a force to the blood vessel that causes the blood vessel to assume an elliptical cross-sectional shape during the at least a portion of diastole.

For some applications, the motor includes a structure that is adapted to press a wall of the blood vessel so as to deform the blood vessel, and one or more protective elements, adapted to provide a protective interface between the structure and the wall of the blood vessel.

There is yet additionally provided, in accordance with an embodiment of the present invention, apparatus for applying counterpulsation treatment to a subject, the apparatus including:

a frame, adapted to be inserted into a blood vessel of the subject carrying oxygenated blood, and to be positioned such that at least a portion of the frame is in mechanical communication with the blood vessel; and a motor, coupled to the frame, and adapted to apply, during at least a portion of diastole, a diastolic force to the frame that causes the portion of the frame to cause the blood vessel to assume an elliptical cross-sectional shape during the at least a portion of diastole.

There is also provided, in accordance with an embodiment of the present invention, apparatus including:

an implantable counterpulsation device, adapted to be coupled to a pulmonary vein of a subject; and a valve, adapted to be implanted in the pulmonary vein, and configured to bias blood flow in the pulmonary vein towards a left atrium of the subject.

For some applications, the valve is integrated into the counterpulsation device.

For some applications, the apparatus is configured to treat diastolic heart failure of the subject.

There is further provided, in accordance with an embodiment of the present invention, apparatus including:

an implantable counterpulsation device, having a first opening and a second opening;

a first conduit and a second conduit, coupled to the first opening and the second opening, respectively; and a common conduit, coupled to the first conduit and the second conduit, and adapted to be coupled by anastomosis to a site of an artery of a subject.

For some applications, the apparatus includes a valve, configured to bias blood flow unidirectionally through the first conduit and the second conduit. Alternatively or additionally, the apparatus includes a flap, configured to bias blood flow unidirectionally through the first conduit and the second conduit.

For some applications, the artery includes a left subclavian artery of the subject, and the common conduit is adapted to be coupled to the left subclavian artery.

There is still further provided, in accordance with an embodiment of the present invention, a method for using an inflatable bladder, including:

coupling the bladder to a blood vessel of a subject carrying oxygenated blood, such that an interior of the bladder is in fluid communication with the blood;

synchronizing contraction and expansion of the bladder with a cardiac cycle of the subject by applying a motor-generated force to a piston in mechanical communication with the bladder; and applying a spring-generated force to the piston.

For some applications, synchronizing includes sensing a physiological parameter of the subject, and synchronizing the contraction and the expansion of the bladder responsive to the sensed parameter.

There is additionally provided, in accordance with an embodiment of the present invention, a method including coupling by anastomosis an implantable counterpulsation device to a blood vessel of a subject carrying oxygenated blood, the device having a motor, adapted to apply force to oxygenated blood of a subject during diastole, and a spring, adapted to store energy received from the oxygenated blood during systole, and to return the stored energy to the oxygenated blood during diastole.

There is yet additionally provided, in accordance with an embodiment of the present invention, a method for applying counterpulsation treatment to a subject, including:

determining an occurrence of diastole by detecting blood pressure applied to a motor;

responsive to the determination, driving the motor to apply force to oxygenated blood of the subject during diastole;

storing, in a spring, energy received from the blood during systole; and returning the stored energy to the blood during diastole.

There is also provided, in accordance with an embodiment of the present invention, a method for applying counterpulsation treatment to a subject, including:

storing, in a spring, energy received from oxygenated blood of the subject during systole;

returning the stored energy to the blood during diastole;

determining an occurrence of diastole by detecting blood pressure applied to the spring; and responsive to the determination, driving a motor to apply force to the blood during diastole.

There is further provided, in accordance with an embodiment of the present invention, a method for using an inflatable bladder having an inner layer and an outer layer, which define a chamber therebetween, the method including:

implanting the bladder in a subject such that an interior of the bladder defined by the inner layer is in fluid communication with blood of a blood vessel of the subject; and detecting an electrical current in the chamber.

There is still further provided, in accordance with an embodiment of the present invention, a method for using an inflatable bladder having an inner layer and an outer layer, which define a chamber therebetween, the method including:

implanting the bladder in a subject such that an interior of the bladder defined by the inner layer is in fluid communication with blood of a blood vessel of the subject; and detecting an electrical current between the chamber and extracellular fluid of the subject.

There is additionally provided, in accordance with an embodiment of the present invention, a method for applying counterpulsation treatment to a subject, the method including inserting, into a blood vessel of the subject carrying oxygenated blood, one or more springs configured to cause the blood vessel to assume an elliptical cross-sectional shape during at least a portion of diastole.

There is yet additionally provided, in accordance with an embodiment of the present invention, a method for applying counterpulsation treatment to a subject, the method including inserting, into a blood vessel of the subject carrying oxygenated blood, one or more springs configured to cause the blood vessel to assume, during at least a portion of diastole, a spring-induced cross-sectional area that is less than a spring-absent cross-sectional area of the blood vessel in the absence of the springs during the portion of diastole.

There is also provided, in accordance with an embodiment of the present invention, a method for applying counterpulsation treatment to a subject, the method including:

inserting a frame into a blood vessel of the subject carrying oxygenated blood;

positioning the frame such that at least two portions of the frame are in mechanical communication with the blood vessel; and during at least a portion of diastole, applying a force to the frame that causes the portions of the frame to cause the blood vessel to assume an elliptical cross-sectional shape during the at least a portion of diastole.

There is further provided, in accordance with an embodiment of the present invention, a method for applying counterpulsation treatment to a subject, the method including:

inserting a frame into a blood vessel of the subject carrying oxygenated blood;

positioning the frame such that at least a portion of the frame is in mechanical communication with the blood vessel; and applying a force to the frame that causes the portion of the frame to cause the blood vessel to assume, during at least a portion of diastole, a frame-induced cross-sectional area that is less than a frame-absent cross-sectional area of the blood vessel in the absence of the frame during the at least a portion of diastole.

There is still further provided, in accordance with an embodiment of the present invention, a method for applying counterpulsation treatment to a subject, the method including:

inserting a motor into a blood vessel of the subject carrying oxygenated blood; and driving the motor to apply, during at least a portion of diastole, a force to the blood vessel that causes the blood vessel to assume an elliptical cross-sectional shape during the at least a portion of diastole.

There is additionally provided, in accordance with an embodiment of the present invention, a method for applying counterpulsation treatment to a subject, the method including:

inserting a frame into a blood vessel of the subject carrying oxygenated blood;

positioning the frame such that at least a portion of the frame is in mechanical communication with the blood vessel; and during at least a portion of diastole, applying a force to the frame that causes the portion of the frame to cause the blood vessel to assume an elliptical cross-sectional shape during the at least a portion of diastole.

There is yet additionally provided, in accordance with an embodiment of the present invention, a method including:

coupling a counterpulsation device to a pulmonary vein of a subject; and implanting a valve in the pulmonary vein, the valve configured to bias blood flow in the pulmonary vein towards a left atrium of the subject.

There is still additionally provided, in accordance with an embodiment of the present invention, a method for implanting a counterpulsation device having a first opening and a second opening, and a first conduit and a second conduit, coupled to the first opening and the second opening, respectively, and a common conduit, coupled to the first conduit and the second conduit, the method including coupling, by anastomosis, the common conduit to a site of an artery of a subject.

There is further provided, in accordance with an embodiment of the present invention, a method for treating a subject, including coupling a counterpulsation device to a left subclavian artery of the subject via a single opening in the artery, without coupling the device to any other blood vessel of the subject.

There is still further provided, in accordance with an embodiment of the present invention, a method for applying counterpulsation treatment to a subject, the method including:

detecting an indication of a compliance of a blood vessel of the subject carrying oxygenated blood;

selecting at least one spring responsive to the indication; and inserting the selected spring into the blood vessel, so as to apply the counterpulsation treatment.

For some applications, selecting the at least one spring includes selecting the at least one spring at least in part responsively to a spring constant of the at least one spring.

The present invention will be more fully understood from the following detailed description of embodiments thereof, taken together with the drawings, in which:

BRIEF DESCRIPTION OF THE DRAWINGS

FIGS. 2A and 2B are schematic illustrations of a cardiac recovery device, in accordance with an embodiment of the present invention;

FIGS. 17A and 17B are schematic illustrations of yet another motorized counterpulsation system during systole and the middle of diastole, respectively, in accordance with an embodiment of the present invention;

DETAILED DESCRIPTION OF EMBODIMENTS

Figure 1A:
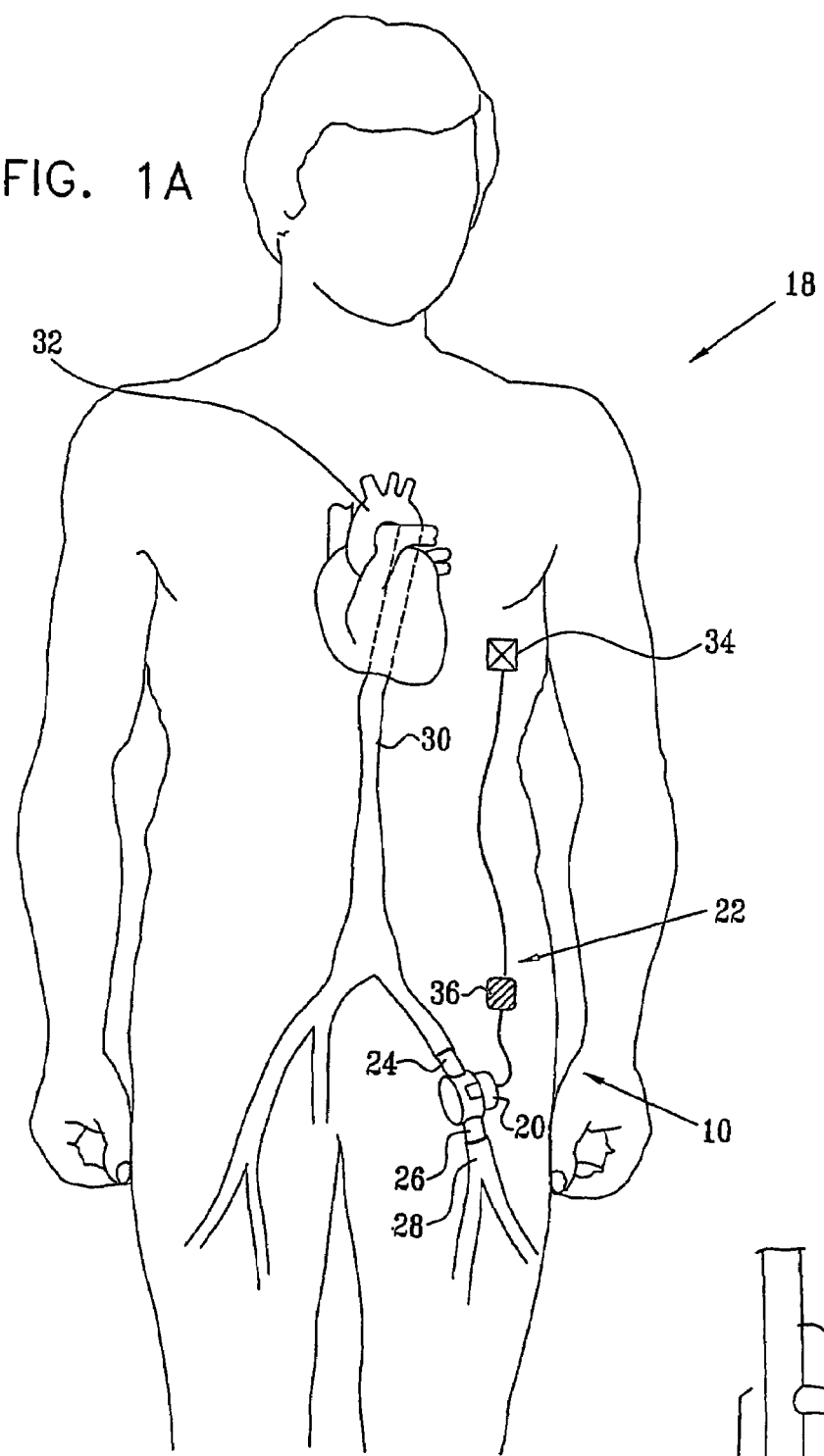
FIG. 1A is a pictorial view of a cardiac recovery system implanted in a subject, in accordance with an embodiment of the present invention.

FIG. 1A is a pictorial view of a cardiac recovery system 10, comprising a cardiac recovery device 20 implanted in a blood vessel 22 on the arterial side of the circulation of a subject 18, in accordance with an embodiment of the present invention. Device 20 is generally implanted in arterial blood vessel 22 during a simple surgical procedure in which the artery is cut, and respective cut ends of the artery are attached to an inflow conduit 24 and an outflow conduit 26 of the device, so that blood flowing through the artery passes through device 20. Device 20 is typically implanted in an iliac artery 28, a descending aorta 30, an ascending aorta 32, or another peripheral artery of subject 18, such as a femoral artery. For some applications, system 10 comprises an implanted or external control unit 36, and one or more implantable or external sensors 34, which are typically adapted to generate an electrocardiogram (ECG) signal.

Figure 1B:
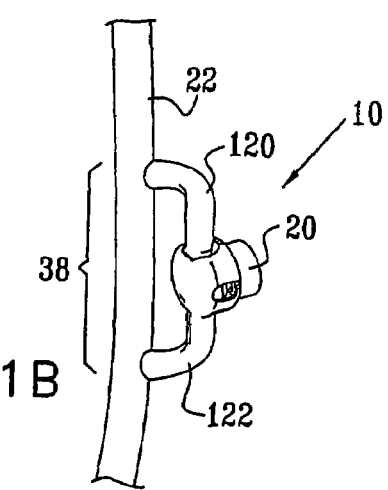
FIG. 1B is a pictorial view of an alternative implantation configuration of the system of FIG. 1A, in accordance with an embodiment of the present invention.

FIG. 1B is a pictorial view of an alternative implantation configuration of system 10, in accordance with an embodiment of the present invention. In this configuration, system 10 additionally comprises an input conduit 120 and an output conduit 122. System 10 is implanted in parallel with arterial blood vessel 22, so that a portion of the blood flowing through the blood vessel continues to flow through a section 38 of the blood vessel, while another portion is diverted, via input conduit 120, through device 20, and back to the blood vessel via output conduit 122.

It is to be understood that whereas conduits 120 and 122 are described as being input and output conduits, respectively, for some applications each of the conduits serves as both an input conduit during systole, and as an output conduit during diastole.

It is additionally to be understood that whereas two conduits are shown in FIG. 1B (and in other figures), the scope of the present invention includes the use of a single conduit, through which blood flows towards device 20 during systole and away from device 20 during diastole.

Figure 1C:
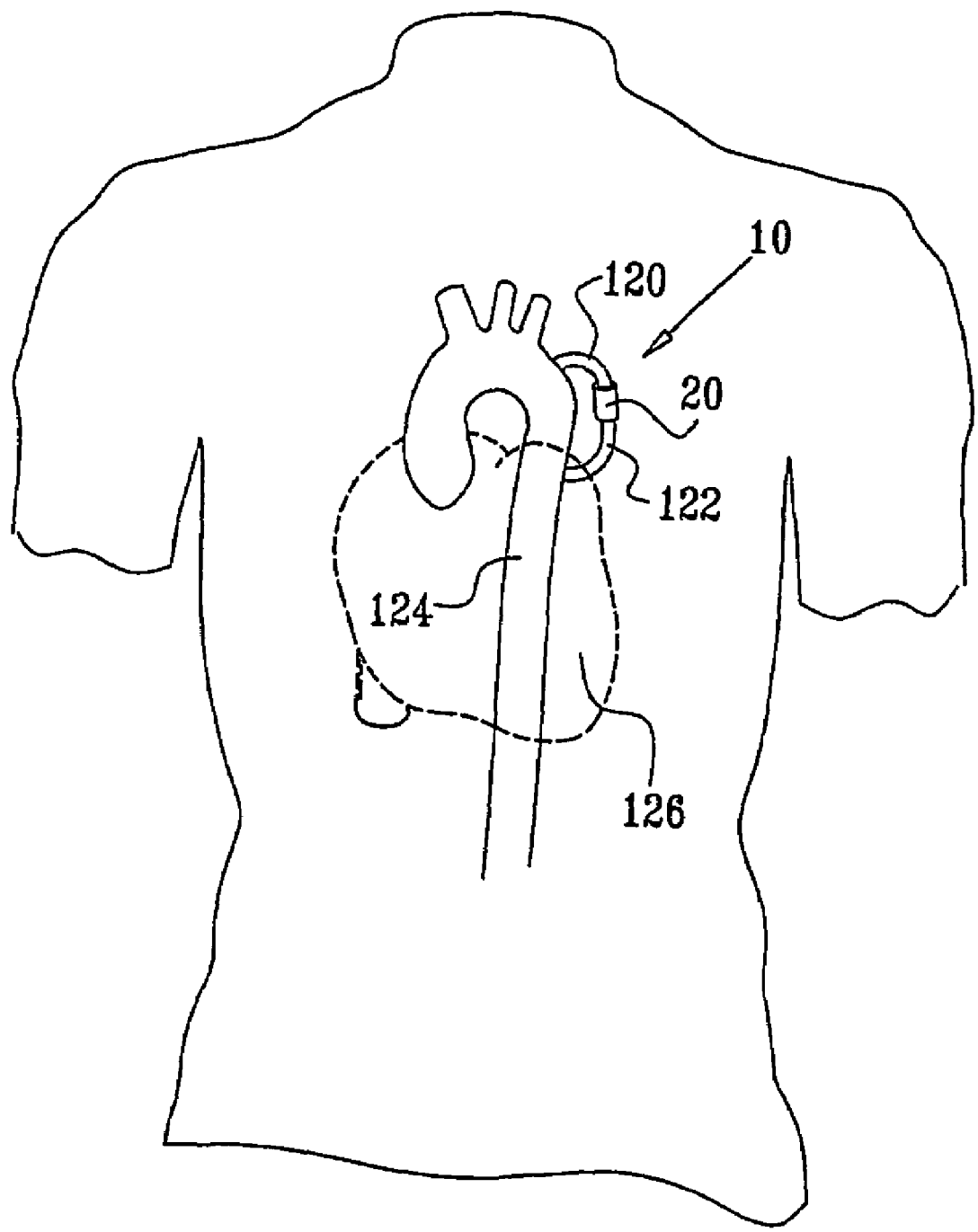
FIG. 1C is a pictorial view of an implantation of the system of FIG. 1A parallel to a descending thoracic aorta, in accordance with an embodiment of the present invention.

FIG. 1C is a pictorial view of an implantation of system 10 parallel to a descending thoracic aorta 124, in accordance with an embodiment of the present invention. System 10 is implanted in parallel with descending thoracic aorta 124 (which is shown passing behind a heart 126), so that a portion of the blood flowing through the descending thoracic aorta continues to flow through the descending thoracic aorta, while another portion is diverted through system 10. For some applications, conduits 120 and 122 are coupled to descending thoracic aorta 124 using side bite clamping or other techniques known in the art, which may obviate the need for cardiopulmonary bypass.

Figure 1D:
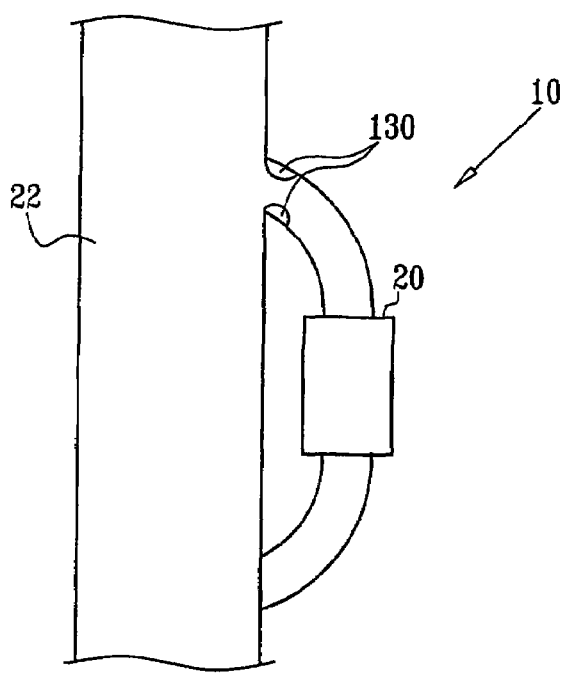
FIG. 1D is a pictorial view of the system of FIG. 1A comprising a constriction element, in accordance with an embodiment of the present invention.

FIG. 1D is a pictorial view of system 10 comprising a constriction element 130, in accordance with an embodiment of the present invention. Constriction element 130 typically causes asymmetric blood flow through system 10, i.e., a partial biasing of the flow towards unidirectional flow through device 20. For some applications, constriction element 130 is adjustable, such as by a motor (configuration not shown), while for other applications, the constriction element is fixed. In an embodiment, constriction element 130 comprises a valve.

Figure 1E:
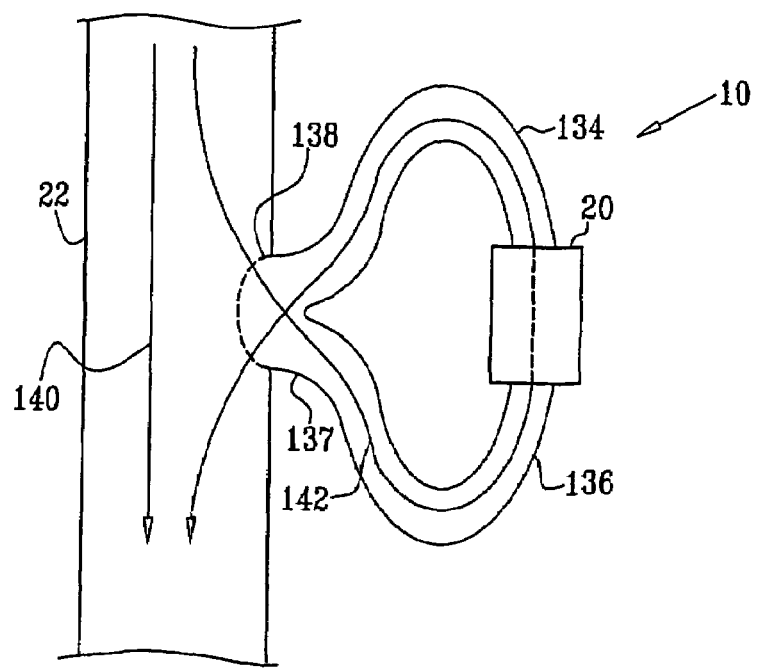
FIGS. 1E-G are pictorial views of alternate configurations of the system of FIG. 1A, in accordance with respective embodiments of the present invention.
Figure 1F:
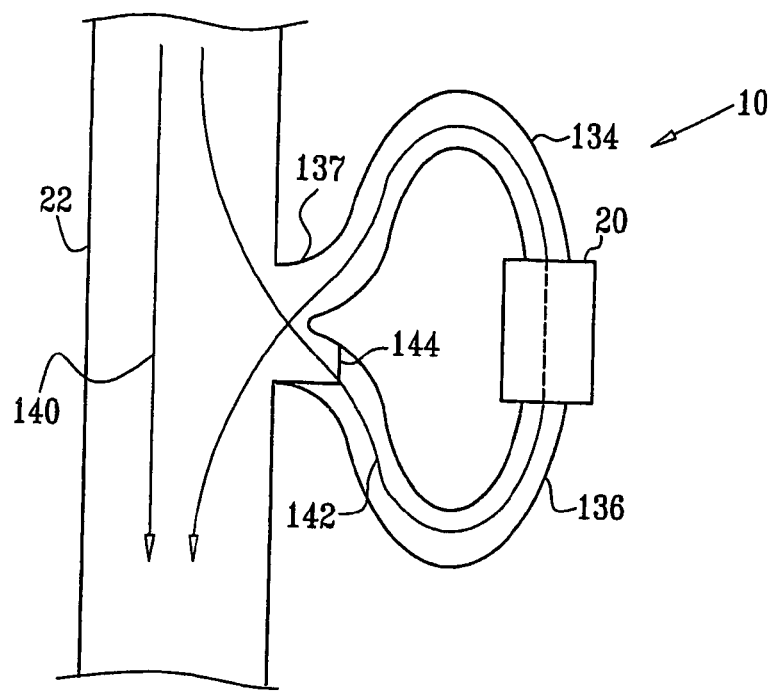
Figure 1G:
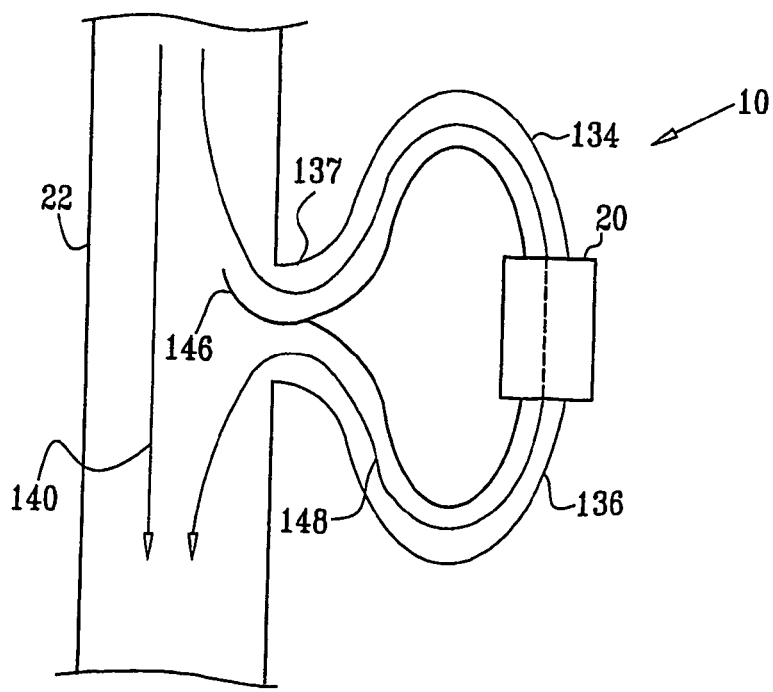

FIGS. 1E-G are pictorial views of alternate configurations of system 10, in accordance with respective embodiments of the present invention. In these configurations, system 10 comprises device 20 and connecting conduits 134 and 136, which are coupled to a common conduit 137 in a vicinity of a single opening 138 with blood vessel 22, to which common conduit 137 is coupled, typically by anastomosis, either with or without sutures. In this configuration, a portion of the blood flowing through blood vessel 22 is diverted through system 10, while another portion of the blood continues to flow through blood vessel 22, as indicated by an arrow 140. For some applications, techniques described in one or more of the above-cited Landesberg patents or patent application are adapted for use with this procedure, or for use with other procedures described herein.

In the configurations shown in FIGS. 1E and 1F, the portion of the blood diverted through system 10 typically flows in the direction indicated by an arrow 142. In the configuration shown in FIG. 1E, such directional blood flow occurs because of the configuration and orientation of system 10 with respect to blood vessel 22. In the configuration shown in FIG. 1F, system 10 additionally comprises a valve 144, which reinforces the directional bias of the blood flow. Typically, valve 144 is open during systole, allowing blood to flow through conduit 136 into device 20. During diastole, the valve closes, causing blood expelled from device 20 to flow through conduit 134. For some applications, a valve is also provided in conduit 134 to yet further support the directional bias of the blood flow. In the configuration shown in FIG. 1G, system 10 comprises a flap 146 that directs blood to flow through system 10 generally in the direction indicated by an arrow 148.

Figure 1H:
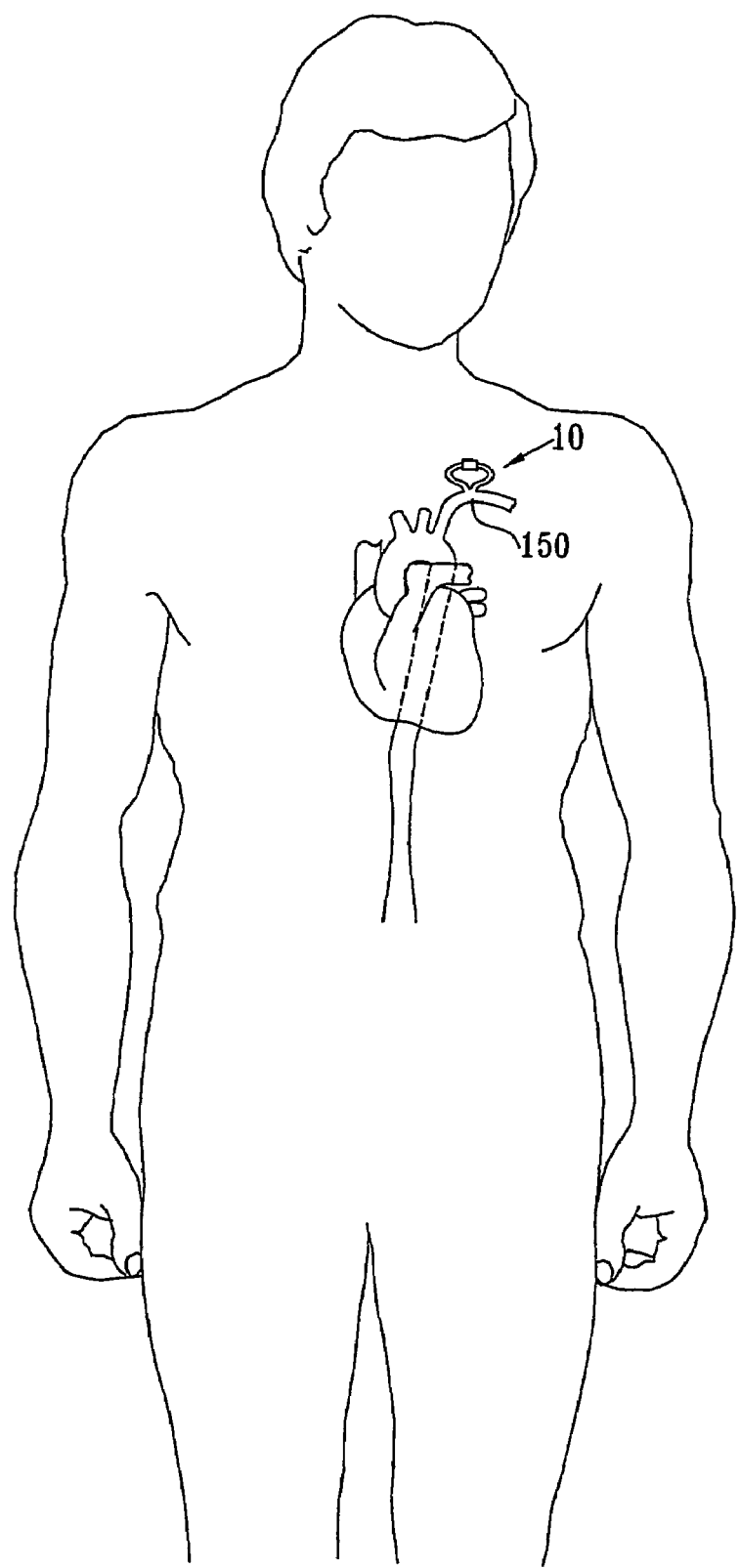
FIG. 1H is a pictorial view of the system of FIG. 1A coupled to a left subclavian artery, in accordance with an embodiment of the present invention.

FIG. 1H is a pictorial view of system 10 coupled to a left subclavian artery 150, in accordance with an embodiment of the present invention. When implanted at this location, system 10 typically has the single-opening configuration described hereinabove with reference to FIGS. 1E-G. Access to left subclavian artery 150 is generally adequate to enable straightforward implantation of system 10 in its single-opening configuration.

FIGS. 2A and 2B are schematic illustrations of cardiac recovery device 20, in accordance with an embodiment of the present invention. As best seen in FIG. 2A, device 20 comprises an inflatable bladder 40, which comprises either a flexible, non-elastic material, or an elastic material, as described hereinbelow. For some applications, bladder 40 comprises ChronoFlex® AR (CardioTech International, Inc.) or a similar material. Bladder 40 typically comprises a lining, and/or is internally coated with cells taken from subject 18. The lining typically comprises Dacron®, polyurethane, silicone, a mix of silicone and polyurethane, or other suitable biocompatible materials. Bladder 40 typically holds between about 10 and 100 milliliters, such as about 40 milliliters, when in a fully expanded position, and less than about 50% (e.g., about 10%) of this volume when contracted to the ordinary diameter of arterial blood vessel 22. For some applications, bladder 40 is adjustable to hold a volume when contracted that represents greater than 50% of the expanded volume, such as between about 50% and about 80% of the expanded volume.

Figure 3A:
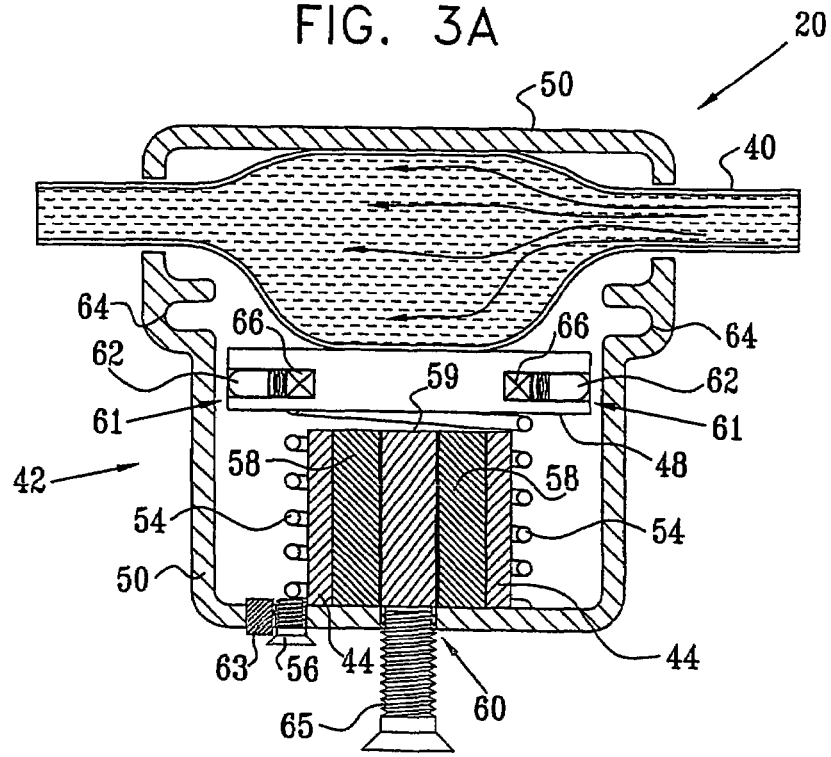
FIGS. 3A and 3B are schematic cross-sectional views of the device of FIGS. 2A and 2B, in accordance with an embodiment of the present invention.
Figure 3B:
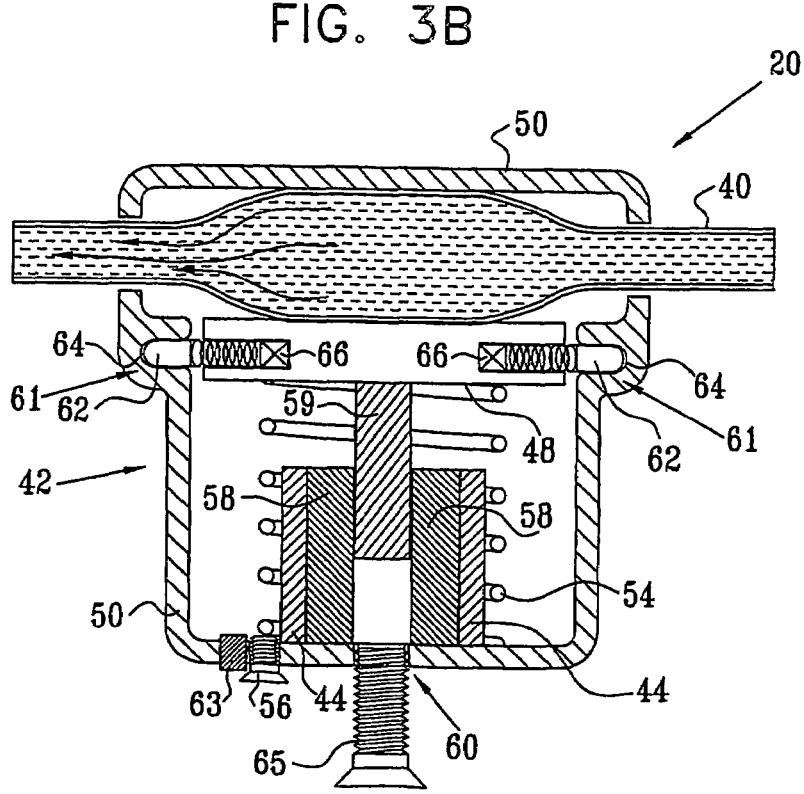

Reference is now made to FIGS. 2A, 2B, 3A, and 3B. FIGS. 3A and 3B are schematic cross-sectional views of device 20, in accordance with an embodiment of the present invention. FIG. 3A shows piston 48 positioned so that bladder 40 is partially expanded, while FIG. 3B shows the piston positioned so that the bladder is contracted towards the ordinary diameter of arterial blood vessel 22. The top of case 50 is shown preventing bladder 40 from expanding in a direction opposite piston 48.

For some applications, cardiac recovery device 20 additionally comprises a regulation unit 42, which is adapted to regulate and synchronize the contraction and expansion of bladder 40 with the cardiac cycle, as described hereinbelow. The regulation unit typically comprises a support element 44, which in some embodiments is slidably coupled to a sliding rod 46 (which may have the shape of a hollow cylinder). Alternatively or additionally, as shown in FIGS. 3A and 3B, a sliding element 59 is fixed to or in contact with a piston 48, which comes in contact with an external surface of bladder 40 in order to apply pressure to the bladder. In an embodiment, sliding element 59 is physically attached to piston 48, and is therefore able to pull the piston to allow expansion of bladder 40, as well as to push the piston to contract the bladder. For some applications, piston 48 is physically attached to bladder 40, and the piston is actively pulled down before and/or during systole, so as to enhance the rapid drop of aortic pressure. In another embodiment, sliding element 59 is not physically attached to piston 48 (as shown), and is therefore able to separate from piston 48 during portions of its travel. In this latter embodiment, sliding element 59 pushes but does not pull piston 48.

As seen in FIG. 2B, regulation unit 42 typically further comprises a fixed case 50, which is adapted to limit the expansion of bladder 40 in a direction opposite that of regulation unit 42, so as to allow the expansion of the bladder to be regulated by piston 48. Case 50 is typically secured to an end 52 of regulation unit 42 (FIG. 2A) that is further from bladder 40. Device 20, including case 50, typically has a diameter D of between about 3 cm and about 6 cm, and a height H of between about 3 cm and about 6 cm (FIG. 2B). These dimensions typically vary based on the volume of bladder 40. Typically, when bladder 40 has a volume of about 40 milliliters, the diameter and height of device 20 are both about 4.5 cm.

Regulation unit 42 typically comprises a spring 54, which is configured to apply upward pressure on piston 48 directly (as shown) or through an intermediate element (not shown). The spring is typically secured to end 52 of regulation unit 42. For some applications, spring 54 is adjustable. For example, the position of spring 54 may be slidably adjustable along an axis of support element 44, so as to adjust the pressure applied by the spring on the piston and/or the downward distance the piston can travel before encountering resistance from the spring. Alternatively or additionally, spring 54 is adjusted by tightening or loosening a spring screw 56 that presses against the bottom of the spring. The spring is typically adjustable manually, such as by a surgeon, either prior to implantation or during a generally minor surgical procedure after implantation, in order to change the magnitude of the applied treatment. Alternatively, a surgeon can replace the spring with another spring characterized by a different spring constant. Alternatively or additionally, the spring is adjustable automatically, such as by an adjustment motor 63 driven by control unit 36 to adjust the position of the spring. For some applications, spring 54 comprises titanium.

For some applications in which spring 54 is automatically adjustable, control unit 36 periodically adjusts the position of the spring responsive to a spring-adjustment protocol. For example, the control unit may adjust the spring based on the time of day, so as to achieve a level of blood pressure regulation that varies throughout a 24-hour period. Alternatively or additionally, the control unit may adjust the spring based on physiological parameters of the subject, such as (a) blood pressure, as measured by sensing movements of bladder 40, (b) heart rate or other features of an ECG, typically determined using sensors 34, or (c) motion or activity of the subject, such as determined using an accelerometer, as described hereinbelow with reference to FIG. 4.

For some applications, regulation unit 42 comprises at least one motor 60, typically a linear motor, such as a linear stepper motor, which generally allows full control of timing, rate, and expansion volume of bladder 40. Alternatively, for some applications, a direct drive motor or a magnetic motor is used. The motor typically comprises sliding element 59, which is driven by a stator 58. Sliding element 59 typically applies force directly to piston 48, and, for some applications, the sliding element is fixed to the piston. Alternatively, sliding element 59 applies force to the piston using other configurations readily apparent to those skilled in the art, having read the present patent application. For some applications, motor 60 comprises a linear motor such as model number NCM10-30-150-2X manufactured by H2W Technologies, which enables a fully-controllable 1 inch stroke.

In an embodiment of the present invention, regulation unit 42 comprises a piston adjustment screw 65, the end of which prevents further downward motion of sliding element 59.

When tightened sufficiently, the screw causes sliding element 59 to partially prevent the retraction of piston 48, thereby partially preventing the expansion of bladder 40. In an embodiment, another adjustment motor 63 (not shown) is activated to withdraw piston adjustment screw 65 from case 50 to facilitate a greater level of cardiac support by system 10. Typically, this activation is performed during periods of greater systemic or coronary oxygen demand, such as during physical activity of subject 18. Alternatively, the end of adjustment screw 65 is in contact with stator 58; tightening the screw raises the entire motor, thereby partially preventing the retraction of piston 48 and expansion of bladder 40. In an embodiment of the present invention that comprises regulation unit 42, but in which the regulation unit does not comprise motor 60, the end of adjustment screw 65 directly or indirectly partially prevents the retraction of piston 48 and expansion of bladder 40.

For some applications, regulation unit 42 comprises both motor 60 and spring 54, in which case the spring supports the action of the motor, thereby reducing the energy consumption of the motor. For some applications, spring 54 reduces the energy consumption of motor 60 by at least about 80%. Treatment using embodiments of the present invention that comprise regulation unit 42, and in which the regulation unit comprises motor 60 and, optionally, spring 54, is referred to herein as "active treatment." Treatment using embodiments of the present invention that comprise regulation unit 42, and in which the regulation unit comprises spring 54 but not motor 60, is referred to herein as "passive treatment."

It is noted that when motor 60 is not activated, either intentionally, such as when active support is not needed (e.g., during sleep), or unintentionally (e.g., should the battery become fully discharged), passive treatment is still generally applied, unless deliberately deactivated. It is further noted that for some applications, spring 54 may be replaced or supplemented by mechanical compliance elsewhere in system 10, such as in the wall of bladder 40 itself. It is yet further noted that the screws and adjustment motors described herein may be replaced by other means for regulating the position and motion of mechanical elements that are known in the art.

Piston 48, sliding rod 46, sliding element 59, and/or case 50 typically comprises a locking mechanism 61 for locking the piston in place to maintain bladder 40 in its most contracted position, typically for a portion of the cardiac cycle. For example, piston 48 may comprise one or more spring-activated protrusions 62 that engage respective grooves 64 typically defined by an inner surface of case 50, so as to lock the piston in place. To retract the piston and allow the bladder to expand, control circuitry 70 drives actuators 66 to withdraw protrusions 62 from grooves 64. Other locking mechanisms, including placement of protrusions at different locations, will be apparent to those skilled in the art, having read the present patent application, and are considered within the scope of the present invention. Locking mechanism 61 obviates the need for system 10 to expend energy to maintain pressure on bladder 40 in order to hold the bladder in its most contracted position.

System 10 is typically modular in design, so that components of the system can be added, replaced, or removed during a simple surgical procedure. Such a modular design allows the system to be "upgraded," e.g., to convert a passive treatment system to an active treatment system, by replacing only a portion of the components. Such a modular design also enables removal of a portion of the components of the system, e.g., to convert an active system treatment to a passive treatment system, or upon completion of treatment. For example, to minimize the invasiveness of removal surgery, bladder 40 may be left implanted while other components of the system not in direct contact with the systemic blood circulation are removed.

Figure 4:
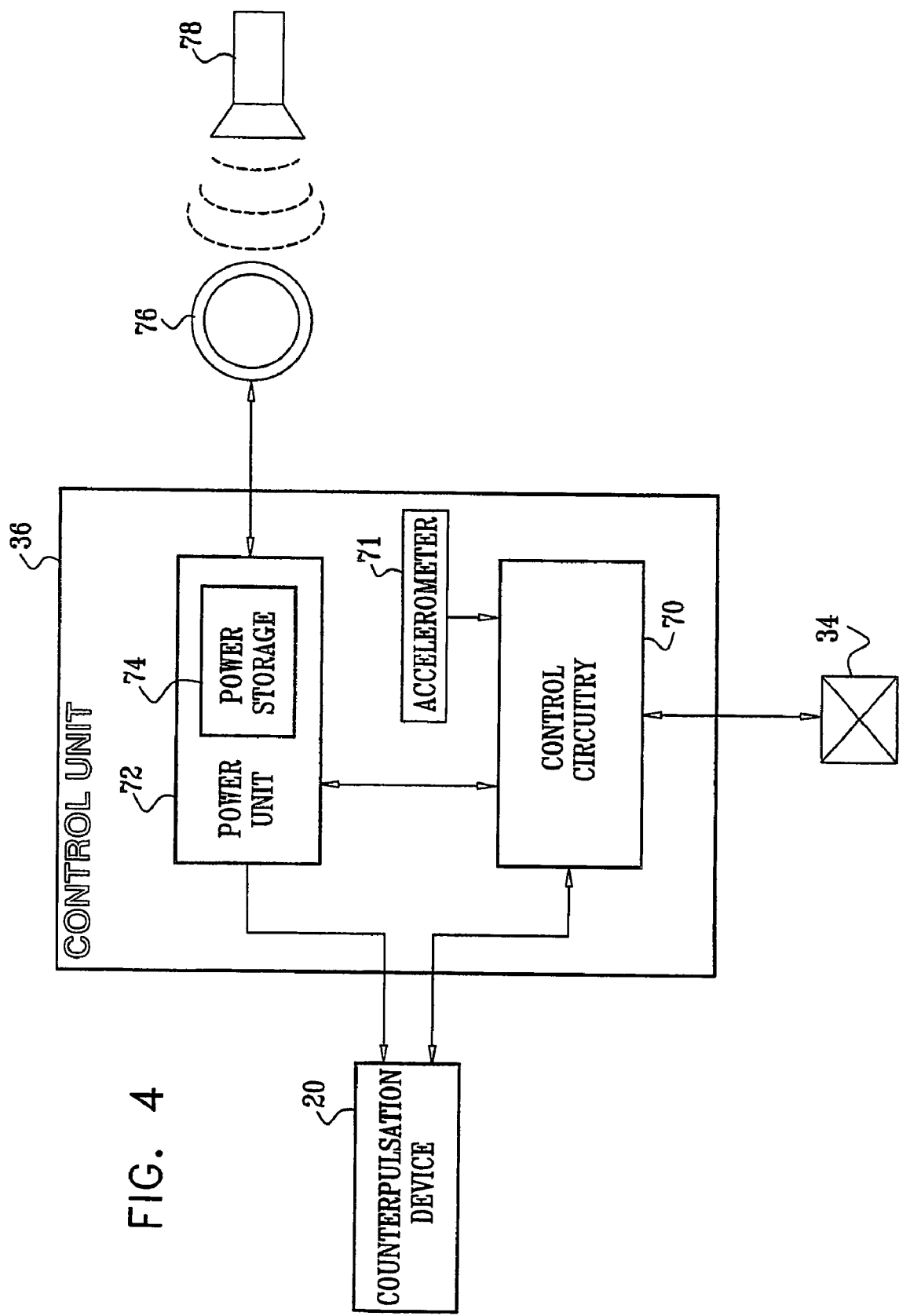
FIG. 4 is a schematic illustration of a control unit of the system of FIG. 1A, in accordance with an embodiment of the present invention.

FIG. 4 is a schematic illustration of control unit 36 and other components of system 10, in accordance with an embodiment of the present invention. Control unit 36 comprises control circuitry 70 and a power unit 72, for powering system 10. Control circuitry 70 controls the operation of system 10, and typically analyzes signals received from external sensors 34 and/or an optional accelerometer 71. The power unit typically comprises a power storage element 74, such as a rechargeable battery. Typically, the power storage element is wirelessly rechargeable from a power source 78 external to the body of the subject. For example, the power storage element may be coupled to an implanted charging coil 76, which receives electromagnetic energy transmitted by the external power source. Alternatively, system 10 is powered by an external power supply connected to power unit 72 over wires (configuration not shown). When regulation unit 42 comprises both motor 60 and spring 54, system 10 typically uses between about 0.1 and about 0.2 watts of power during active treatment, assuming a heart rate of about 60 to 120 beats per minute and a bladder volume of 40 milliliters. One reason why energy consumption is typically so low is that the energy stored in spring 54 allows device 20 to only perform work to increase blood pressure in blood vessel 22 immediately following end-systole. This increase in pressure, from the untreated diastolic blood pressure (typically between 40 and 140 mmHg), is typically approximately 10 to 60 mmHg. In contrast, typical ventricular assist devices (VADs) operating without such a spring must work to increase blood pressure from nearly 0 mmHg to normal diastolic blood pressure, a typical increase of about 120 mmHg.

In an embodiment of the present invention, control circuitry 70 synchronizes the contraction and expansion of bladder 40 with the cardiac cycle in order to apply active treatment to subject 18. The control circuitry drives regulation unit 42 to (a) allow the expansion of bladder 40 immediately prior to systole, thereby accepting blood into the bladder and reducing systemic blood pressure, and (b) actively, and optionally via the spring, contract the bladder during diastole, thereby ejecting the blood from the bladder and increasing systemic diastolic blood pressure. In order to achieve proper cardiac cycle synchronization, one or both of the following parameters are typically monitored:

parameters of an ECG signal, typically as generated by sensors 34. Sensors 34 are typically positioned in extracardiac positions near control unit 36. Alternatively, the sensors are positioned on a surface of or near the heart; and/or arterial blood pressure, as measured directly, typically in bladder 40 (e.g., with a pressure transducer), or indirectly, such as by measuring the position of piston 48, the length of spring 54, or the force in spring 54.

Control circuitry 70 typically analyzes these parameters in order to continuously calibrate the timing of contraction and expansion of bladder 40, by comparing the times of such contraction and expansion with the measured aortic blood pressure responses. The control circuitry typically triggers expansion of the bladder (e.g., by releasing locking mechanism 61, in those embodiments comprising such a mechanism) at a point in time between the P-wave and R-wave of the ECG, and triggers the active contraction of the bladder at a point in time during or soon after the T-wave of the ECG (see the symbolic ECG trace described hereinbelow with reference to FIG. 6). For some applications, this bladder-contraction time point is determined without reference to the ECG signal, by detecting a slight expansion of spring 54 as the spring begins to passively contract the bladder after the aortic valve closes at end-diastole.

For some applications, control circuitry 70 is configured to activate device 20 according to a duty cycle, e.g., every third heart beat. Alternatively or additionally, the control circuitry is configured to only activate the device periodically, such as during certain physiological states of subject 18, e.g., while awake or during exertion or motion. In an embodiment, system 10 has three modes: (a) an active mode for use during physical exertion, in which motor 60 is continuously or intermittently actuated, (b) a passive mode in which passive treatment is applied, for example, during light tasks, and (c) a deactivated mode in which locking mechanism 61 is continuously engaged, for use, for example, during sleep.

Figure 5:
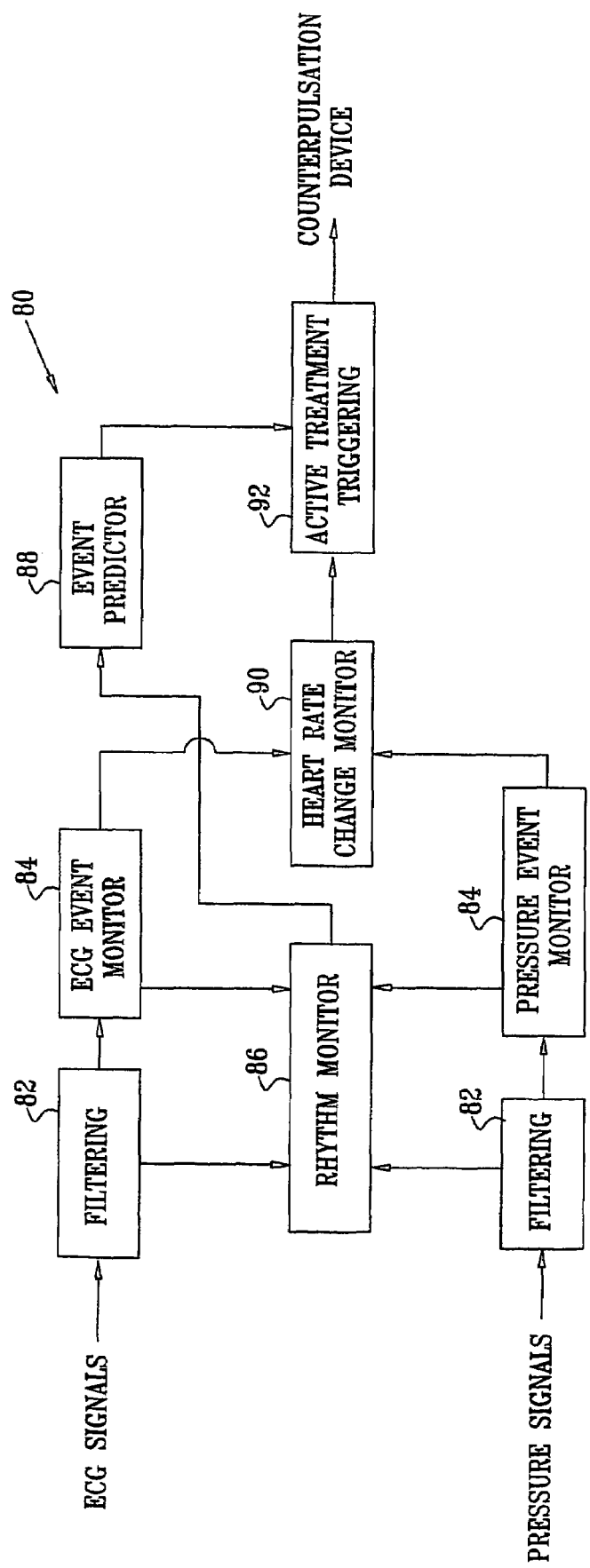
FIG. 5 is a block diagram schematically illustrating a technique for cardiac synchronization, in accordance with an embodiment of the present invention.

FIG. 5 is a block diagram schematically illustrating a technique for synchronization of device 10 with cardiac activity, in accordance with an embodiment of the present invention. Control circuitry 70 typically implements a signal processing mechanism 80 in order to adapt operation of system 10 to irregular heart behavior, which is common in patients suffering from cardiac conditions such as heart failure. Processing mechanism 80 typically comprises the following logical functional units, which are typically programmed in software and/or embodied in hardware to carry out the functions described herein:

- Two adaptive filters 82 (one for ECG signals and the other for pressure signals) filter noise to enable recognition of desired signals, such as P-waves, QRS complexes, T-waves, peak systolic pressure, and end-systolic pressure. The filters typically are configured to adapt to changes in signals that occur as a result of patient activity.
- Two event monitors 84 (one for ECG signals and the other for pressure signals) receive filtered ECG and pressure signals, respectively, and recognize specific heart events by matching the measured signals to predefined definitions or patterns.
- A rhythm monitor 86 correlates the filtered heart activity, including specific recognized heart events, to a parametric model of the heart, in order to define the heart rhythm. The heart rhythm is used to predict heart events (such as electrocardiographic events), to facilitate the proper activation of device 20.
- An event predictor 88 receives input from rhythm monitor 86, and triggers device 20 responsive to specific recognized heart events, and responsive to predicted heart events. The event predictor typically uses an algorithm based on measured heart rhythm in order to predict the timing of heart events.
- A heart rate change monitor 90 receives input from event monitors 84, and determines the occurrence of rapid changes in heart rate, indicating that the predicted rhythm is inaccurate (typically with an accuracy of within 10 ms). This determination is typically made by comparing predicted heart events to measured heart events. When an irregularity is detected, device 20 is typically deactivated until the rhythm is again matched.
- An active treatment triggering unit 92 actuates cardiac recovery device 20 to operate if the heart is behaving as expected.

After an initial calibration period in which heart rate and heart events (such as ECG characteristics) are monitored, a treatment is applied. (In addition, calibration is typically performed substantially continuously during activity of system 10.) Throughout application of the treatment, control circuitry 70 monitors these parameters in real-time to detect actual heart events that differ from heart events predicted based on the calibration. If such an event is detected, control circuitry 70 typically suspends active treatment by system 10 until synchronization is reestablished.

Figure 6:
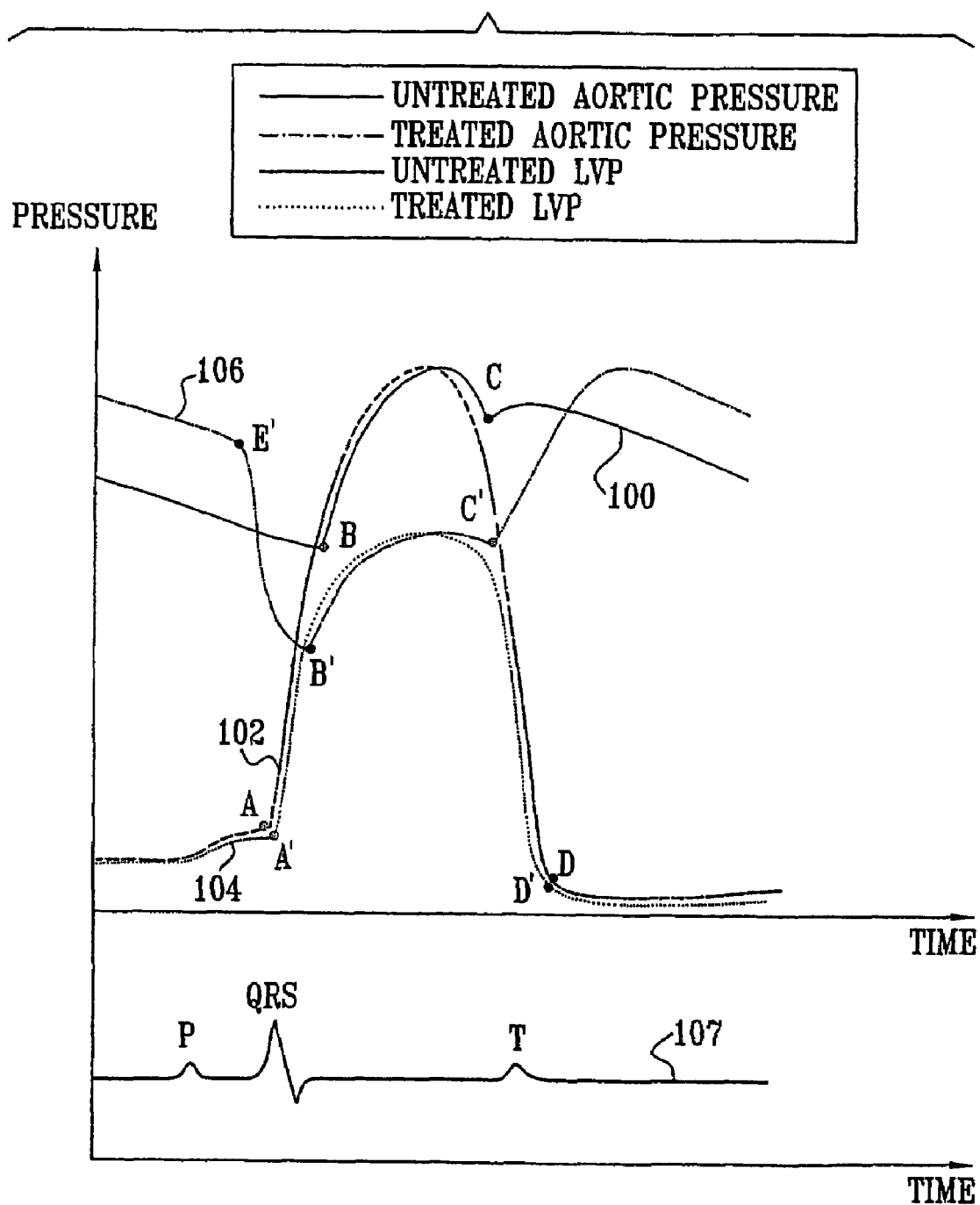
FIG. 6 is a graph showing example pressure curves without treatment and with active treatment by a system like the system of FIG. 1A, in accordance with an embodiment of the present invention.

FIG. 6 is a graph showing example simulated pressure curves without treatment and with active treatment by a system like system 10, in accordance with an embodiment of the present invention. It is emphasized that these pressure curves are exemplary, and reflect assumptions regarding a particular configuration of an embodiment of the present invention and a theoretical subject's reactions to the system. In actual human use, physiological responses are expected to vary substantially from subject to subject, in part dependent upon the particular configuration of the device. Lines 100 and 102 represent the untreated aortic pressure and untreated left ventricular pressure (LVP), respectively, during approximately a single cardiac cycle. Point A represents end-diastole, at which the atrioventricular (A-V) valves close, and the isovolumic contraction phase of systole begins. At point B, LVP exceeds aortic pressure, causing the aortic valve to open, beginning the ejection phase of systole. Point C represents end-systole, when the aortic valve closes. LVP continues to drop until point D, when the A-V valves open.

In an embodiment of the present invention, in order to apply active treatment, control unit 36 regulates blood pressure in synchronization with the cardiac cycle of the subject. During diastole, the treated LVP, as represented by a line 104 between points D' and A' (wrapping around the diagram from the right side to the left side), is approximately the same as the untreated LVP (line 102). However, the treated aortic pressure, represented by a line 106, is elevated compared to the untreated aortic pressure (line 100), as described below. At point E', which typically occurs soon before systole, control unit 36 drives motor 60 to retract, thereby allowing bladder 40 to push piston 48 and expand. The timing of point E' in the cardiac cycle is typically updated intermittently or continuously responsive to calibration data taken during operation of system 10. During early stages of treatment to unload the heart, point E' is typically timed to occur substantially simultaneously with or slightly before the P-wave. During later stages of treatment, after the heart has begun to heal, point E' is typically timed to occur later, sometimes even after point B, in order to gradually load the heart for full pressure.

In some embodiments, retraction of sliding element 59 by motor 60 at point E' automatically retracts piston 48. Alternatively or additionally, in embodiments in which regulation unit 42 comprises locking mechanism 61, the mechanism is disengaged, thereby releasing piston 48. In these embodiments, the aortic pressure is typically sufficient to rapidly depress the piston without the need for assistance from motor 60. For some applications of these embodiments, motor 60 returns sliding element 59 to base position at an earlier point in the cycle after the locking mechanism has been engaged, as described hereinbelow. Bladder 40 expands, accepting blood and rapidly reducing aortic pressure from point E' to point B'. In embodiments in which regulation unit 42 comprises spring 54, the spring is compressed during this phase of operation.

At point B', LVP exceeds aortic pressure, causing the aortic valve to open. Because the aortic pressure at point B' is lower than the aortic pressure at point B, the ejection phase of systole begins at a lower aortic pressure and LVP. This pressure differential (with treatment vs. without treatment) continues through end-systole, at which point the aortic pressure with treatment (point C' on line 106) is lower than the untreated aortic pressure (point C on line 100).

At or soon after end-systole (point C'), control unit 36 drives motor 60 to extend piston 48, thereby compressing bladder 40. The bladder contracts, typically in about 50-100 ms, ejecting the excess blood contained therein, thereby rapidly increasing aortic pressure. In embodiments in which regulation unit 42 comprises spring 54, the spring assists motor 60, releasing energy stored during the transition from E' to B', thereby strengthening the blood ejection and reducing energy consumption by the motor. In embodiments in which regulation unit 42 comprises locking mechanism 61, the mechanism is engaged after the piston has been maximally extended, locking piston 48 against bladder 40. For some applications, upon or soon after such engagement, sliding element 59 of motor 60 returns to base position. As a result of this sudden ejection, soon after systole ends, the treated aortic pressure (line 106) exceeds the untreated aortic pressure (line 100). This elevated aortic diastolic pressure continues until the cardiac cycle returns to point E' and the control unit again retracts the piston, as described above.

The bottom graph of FIG. 6 shows a symbolic ECG trace 107 over the period of the pressure curves. As can be seen, point E', at which bladder 40 begins to rapidly expand, occurs between the P-wave and Q-wave of the ECG. Point C', at which the bladder begins to contract, occurs at or soon after the T-wave of the ECG.

Figure 7:
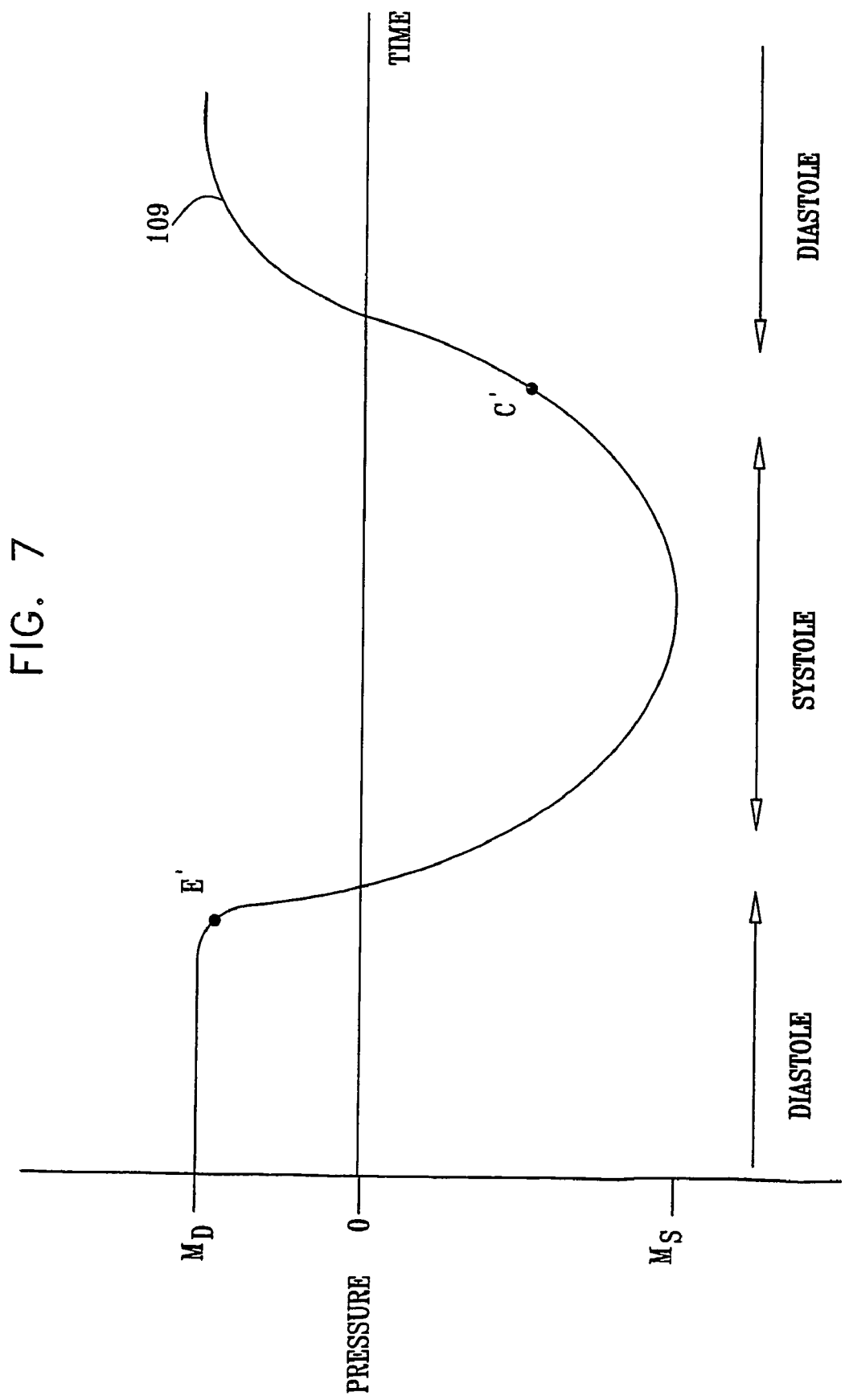
FIG. 7 is a graph showing an example aortic pressure difference curve, in accordance with an embodiment of the present invention.

FIG. 7 is a graph showing an example aortic pressure difference curve, in accordance with an embodiment of the present invention. It is emphasized that this pressure differential curve is exemplary, and reflects assumptions regarding a particular configuration of a system like system 10 and a theoretical subject's reactions to the system. In actual human use, physiological responses are expected to vary substantially from subject to subject, in part dependent upon the particular configuration of the device. A line 109 represents the approximate difference in aortic pressure with active treatment with a system-like system 10 vs. without treatment. Portions of the line above the x-axis indicate times during the cardiac cycle when aortic pressure is greater with active treatment than without treatment, generally corresponding to diastole. The maximum diastolic pressure differential, labeled $M_D$, is typically between about 10 and about 40 mmHg. Portions of the line below the x-axis indicate times during the cardiac cycle when aortic pressure is less with active treatment than without treatment, generally corresponding to systole. The maximum systolic pressure differential, labeled $M_S$, is typically between about 10 and about 40 mmHg. As mentioned above with reference to FIG. 6, at point E', which typically occurs soon before systole, control unit 36 drives motor 60 to retract, thereby allowing bladder 40 to push piston 48 and expand, reducing aortic pressure. At or soon after end-systole (point C'), control unit 36 drives motor 60 to extend piston 48, thereby compressing bladder 40. The bladder contracts, typically in about 50-100 ms, ejecting the excess blood contained therein, thereby rapidly increasing aortic pressure.

Figure 8:
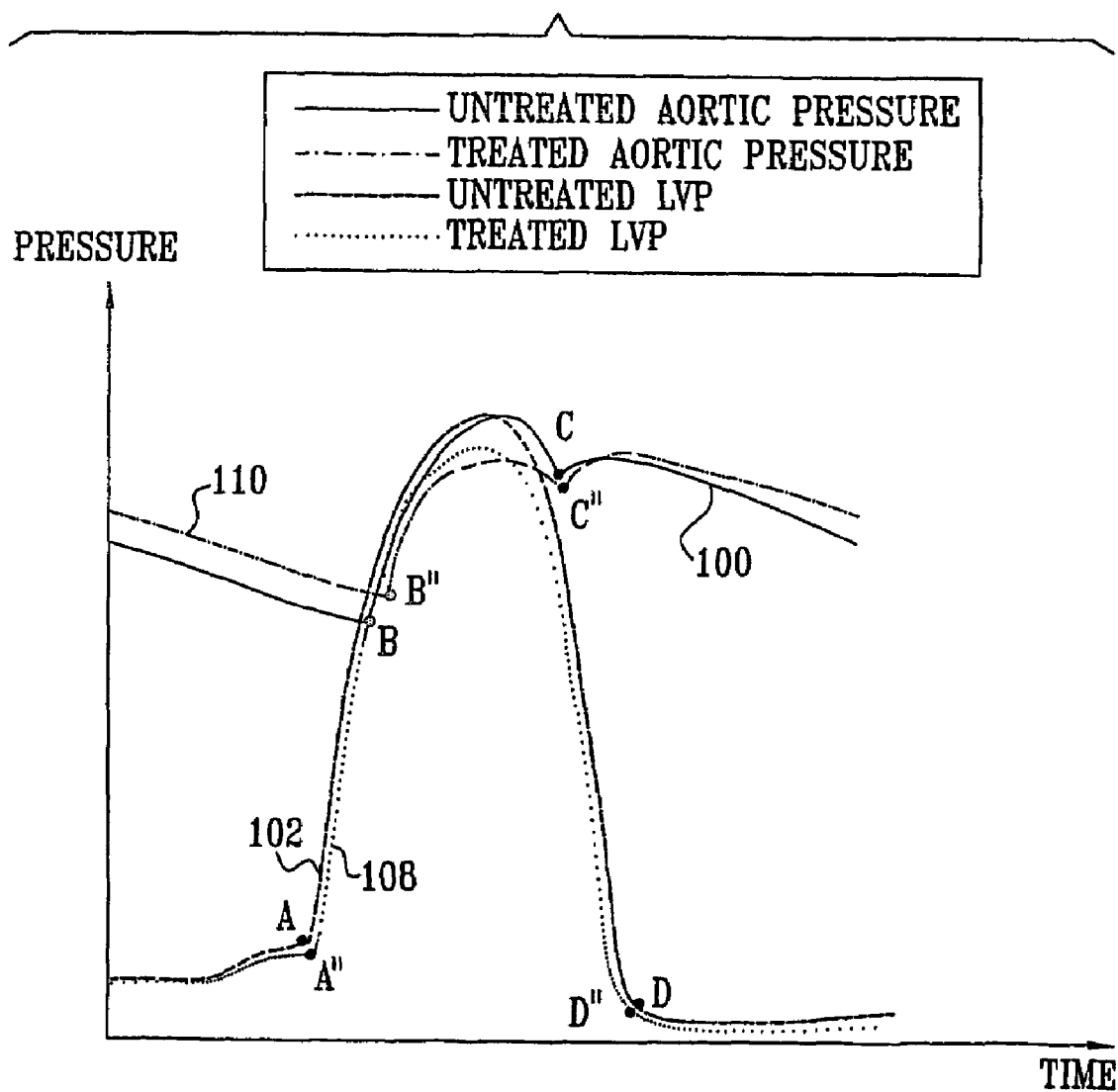
FIG. 8 is a graph showing example pressure curves without treatment and with passive treatment by a system like the system of FIG. 1A, in accordance with an embodiment of the present invention.

Reference is now made to FIG. 8, which is a graph showing example pressure curves without treatment and with passive treatment by a system like system 10, in accordance with an embodiment of the present invention. It is emphasized that these pressure curves are exemplary, and reflect assumptions regarding a particular configuration of a system like system 10 and a theoretical subject's reactions to the system. In actual human use, physiological responses are expected to vary substantially from subject to subject, in part dependent upon the particular configuration of the device. Lines 108 and 110 represent LVP and aortic pressure, respectively, during passive treatment using device 20. Lines 100 and 102 reflect the same example curves without treatment as shown in FIG. 6, and described hereinabove with reference thereto. During diastole, the passively treated LVP, as represented by line 108 between points D" and A" (wrapping around the diagram), is approximately the same as the untreated LVP (line 102). However, the passively treated aortic pressure (line 110) is elevated compared to the untreated aortic pressure (line 100), as described below. At point B", LVP exceeds aortic pressure, causing the aortic valve to open. Because of the higher aortic pressure caused by passive treatment with device 20, the aortic pressure at point B" is higher than the aortic pressure at point B, resulting in the ejection phase of systole beginning at a higher LVP. Commencing at the beginning of the ejection phase of systole, the sudden increase in aortic pressure causes bladder 40 to expand and spring 54 to compress. As a result of the expansion of the bladder, during the ejection phase aortic pressure increases less than it would increase untreated, as is indicated by the position of line 110 below line 100 during systole. Treated LVP (line 108) is also reduced compared to untreated LVP (line 102) during this phase.

At end-systole (point C"), the passively treated aortic pressure (line 110) and untreated aortic pressure (line 100) generally converge. However, as aortic pressure drops in bladder 40, spring 54 experiences less pressure and therefore expands, typically gradually, ejecting some or all of the excess blood accepted by the bladder during the ejection phase of systole. As a result, diastolic aortic pressure is greater than it would be without passive treatment. This elevated aortic pressure continues until the cardiac cycle returns to point B" and the spring again contracts, as described above.

Although a subject passively treated with system 10 experiences moderately increased afterload, the combination of higher diastolic pressure and lower systolic pressure generally serves to treat the heart, more than compensating for any negative effects associated with the moderately increased afterload. As described hereinabove with reference to FIGS. 2A, 2B, 3A, and 3C, in some embodiments passive treatment is adjustable using spring screw 56 or piston adjustment screw 65.

Figure 9:
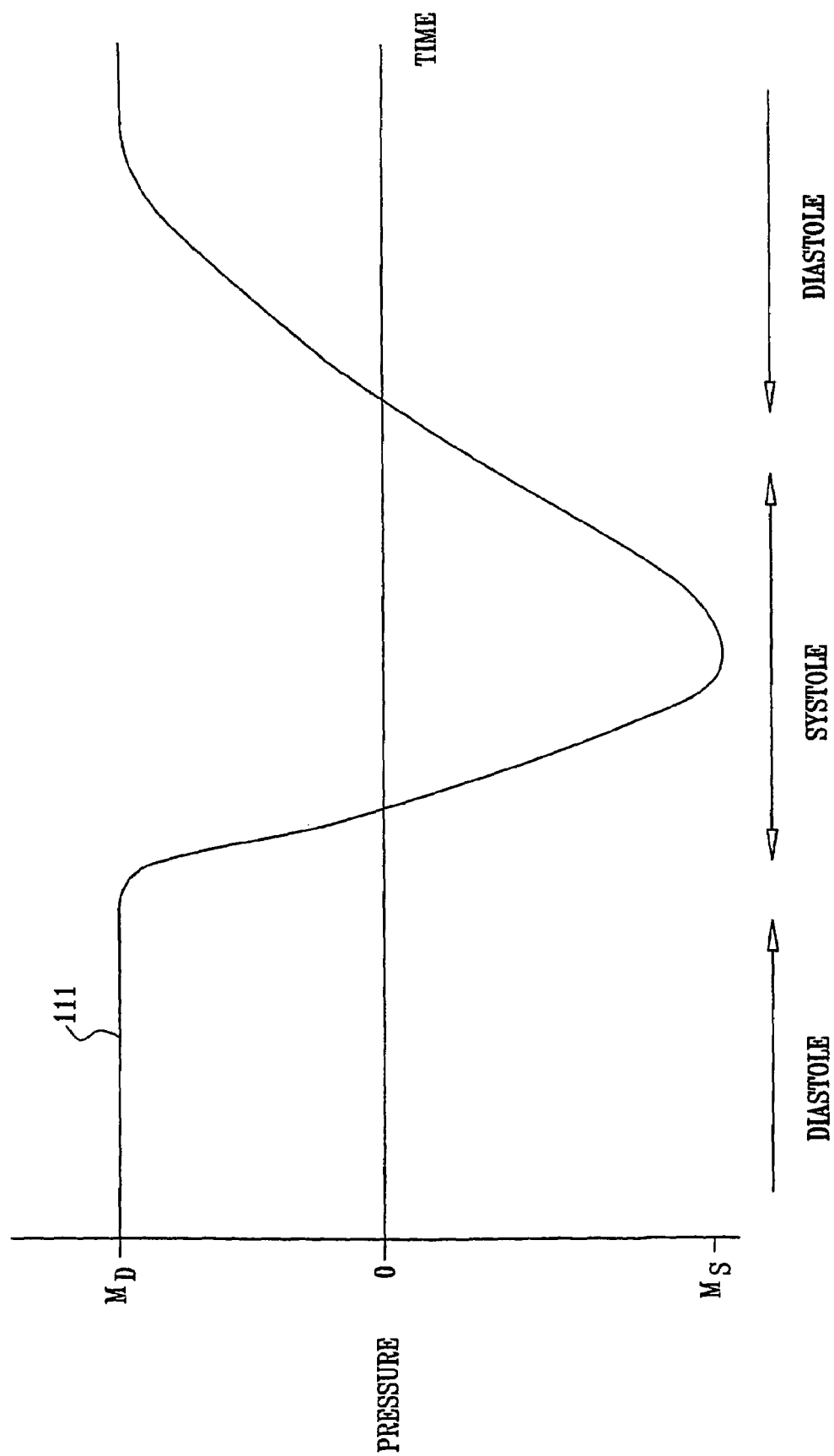
FIG. 9 is a graph showing an example aortic pressure difference curve, in accordance with an embodiment of the present invention.

FIG. 9 is a graph showing an example aortic pressure difference curve, in accordance with an embodiment of the present invention. It is emphasized that this pressure differential curve is exemplary, and reflects assumptions regarding a particular configuration of a system like system 10 and a theoretical subject's reactions to the system. In actual human use, physiological responses are expected to vary substantially from subject to subject, in part dependent upon the particular configuration of the device. A line 111 represents the approximate difference in aortic pressure with passive treatment with a system like system 10 vs. without treatment. Portions of the line above the x-axis indicate times during the cardiac cycle when aortic pressure is greater with passive treatment than without treatment, generally corresponding to diastole. The maximum diastolic pressure differential, labeled $M_D$, is typically between about 10 and about 40 mmHg. Portions of the line below the x-axis indicate times during the cardiac cycle when aortic pressure is less with passive treatment than without treatment, generally corresponding to systole. The maximum systolic pressure differential, labeled $M_S$, is typically between about 10 and about 40 mmHg.

Figure 10:
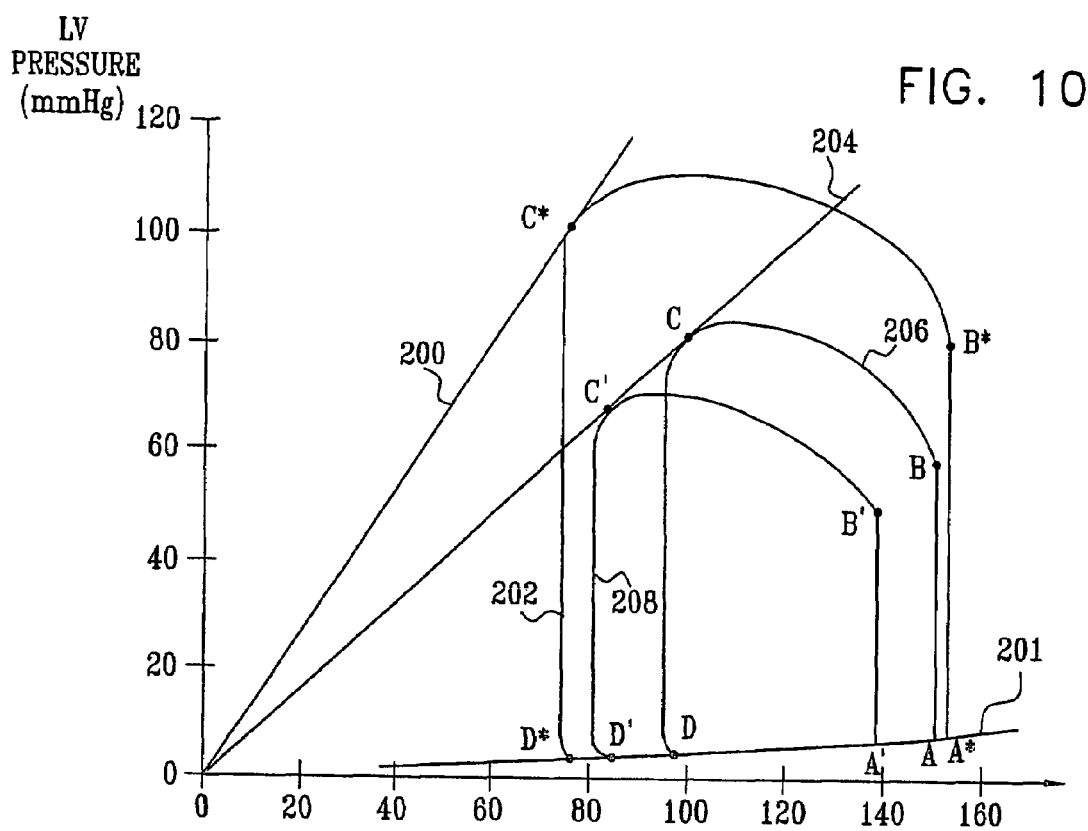
FIG. 10 is a graph showing example pressure-volume (PV) loops illustrating a benefit of active treatment with a system like the system of FIG. 1A, in accordance with an embodiment of the present invention.

FIG. 10 is a graph showing example pressure-volume (PV) loops illustrating a benefit of active treatment with a system like system 10, in accordance with an embodiment of the present invention. It is emphasized that these PV loops are exemplary, and reflect assumptions regarding a particular configuration of a system like system 10 and a theoretical subject's reactions to the system. In actual human use, physiological responses are expected to vary substantially from subject to subject, in part dependent upon the particular configuration of the device. The points on these PV loops labeled A, B, C, D, A', B', C' and D' correspond to the points correspondingly labeled on the pressure curves of FIG. 6. The slope of a line 200 represents the end-systolic elastance (Ees) (indicative of heart contractility) of an example non-diseased heart. This non-diseased heart has a PV loop A*B*C*D* 202, indicative of a stroke volume equal to A*–D*, i.e., approximately 153 ml–75 ml=78 ml, and a left ventricular ejection fraction (LVEF), representing the workload efficiency of the LV, equal to (A*–D*)/A*, i.e., (153 ml–75 ml)/153 ml=0.51. Heart workload, as indicated by the area of the triangle bounded in part by PV loop 202 and the axis origin, is approximately 10,725 mmHg·ml. A curve 201 represents diastolic preload.

The slope of a line 204 represents the Ees of a heart of subject 18 that is suffering from heart failure. Prior to treatment with system 10, subject 18 has PV loop ABCD 206, where end-systole (point C) is bound by Ees line 204. This untreated heart has a stroke volume of 151 ml–95 ml=56 ml, and an LVEF of (151 ml–95 ml)/151 ml=0.37. Heart workload is approximately 7,030 mmHg·ml.

Active treatment with system 10 typically causes the PV loop to widen and have a lower upper pressure boundary, as shown, for example, in a PV loop A'B'C'D' 208. As described hereinabove with reference to FIG. 6, such active treatment reduces afterload, causing LVP to exceed aortic pressure, and the aortic valve to open, at a lower ventricular pressure (point B') than without treatment (point B). The ejection phase of systole remains generally bound in the short term by Ees line 204, but because of the lower LVP when the aortic valve opens, the heart pumps more blood during systole, and therefore ends with a lower LV volume (point C') than without treatment (point C). In this example, active treatment with system 10 increases the stroke volume to 139 ml–81 ml=58 ml, and the LVEF to (139 ml–81 ml)/139 ml=0.42. Active treatment also reduces heart workload in this example to approximately 5,560 mmHg·ml. Reduced heart workload generally enables healing of the heart and improved contractility, which typically results in an improved ejection fraction. The energy applied by the active device typically causes unloading of the heart. Longer term, as the heart heals, the active mode of operation of the device is typically disabled for at least a portion of the time, e.g., every other beat. Such disablement is typically performed gradually, while the heart is still assisted by the passive operation of the device. Typically, such disablement is performed under medical supervision.

Figure 11:
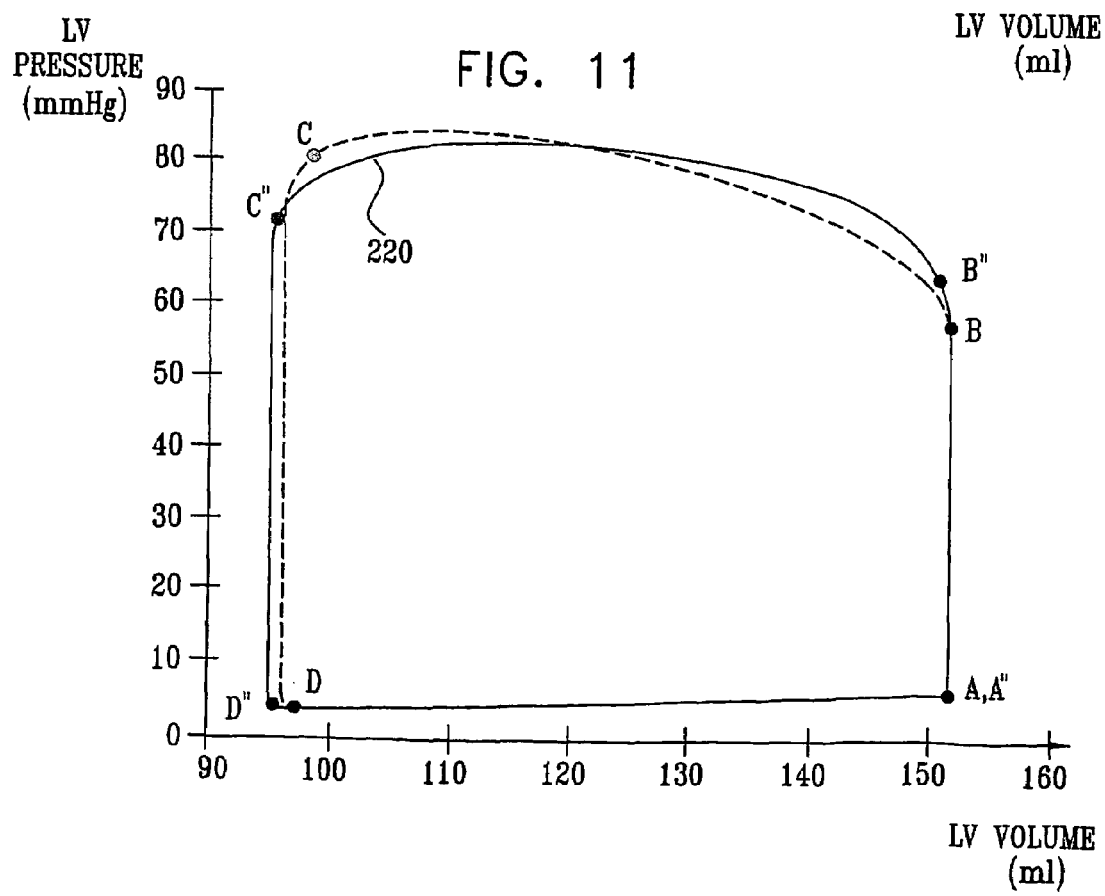
FIG. 11 is a graph showing example pressure-volume (PV) loops illustrating a benefit of passive treatment with a system like the system of FIG. 1A, in accordance with an embodiment of the present invention.

FIG. 11 is a graph showing example pressure-volume (PV) loops illustrating a benefit of passive treatment with a system like system 10, in accordance with an embodiment of the present invention. It is emphasized that these PV loops are exemplary, and reflect assumptions regarding a particular configuration of a system like system 10 and a theoretical subject's reactions to the system. In actual human use, physiological responses are expected to vary substantially from subject to subject, in part dependent upon the particular configuration of the device. The points on these PV loops labeled A, B, C, D, A", B", C" and D" correspond to the points correspondingly labeled on the pressure curves of FIG. 8.

Passive treatment with system 10 typically causes the PV loop to widen, as shown, for example, in a PV loop A"B"C"D" 220. As described hereinabove with reference to FIG. 8, such passive treatment causes the aortic pressure at point B" to be higher than the aortic pressure at point B, resulting in the ejection phase of systole beginning at a higher LVP. For some applications (such as in patients with stiffer arteries), passive treatment with system 10 typically results in about a 5% improvement in ejection fraction, about a 5% improvement in heart work, about a 15% elevation in diastolic blood pressure, and about a 10% decrease in systolic blood pressure. In some patients, it is expected that passive treatment with system 10 alternatively or additionally results in a shift of the entire PV loop to the left (not shown).

As mentioned, the numerical values used in these example PV loops are to be understood as being illustrative only, and do not reflect actual experimental or clinical data, or outcomes achieved in human subjects treated with system 10. In addition, one or both of the following additional improvements are expected to occur, as the heart pumps more blood as a result of the lower ventricular pressure (points B' and B") when the aortic valve opens:

end-diastole (points A' and A") is expected to occur at a lower LV volume, thereby shifting segments A'B' and C'D' (active treatment) or A"B" and C"D" (passive treatment) to the left, while maintaining or increasing stroke volume; and/or as venous pressure declines, preload is expected to decline; such decline is reflected as a reduction in the slope of curve 201.

In addition, although the Ees (the slope of line 204, indicative of contractility) is shown in FIG. 10 as remaining constant during treatment with system 10, such treatment, particularly if long-term, is expected to improve the Ees of some patients (increasing the slope of line 204 towards line 200) by lowering heart stress and/or increasing diastolic pressure, in both active and passive embodiments of the present invention.

Figure 12:
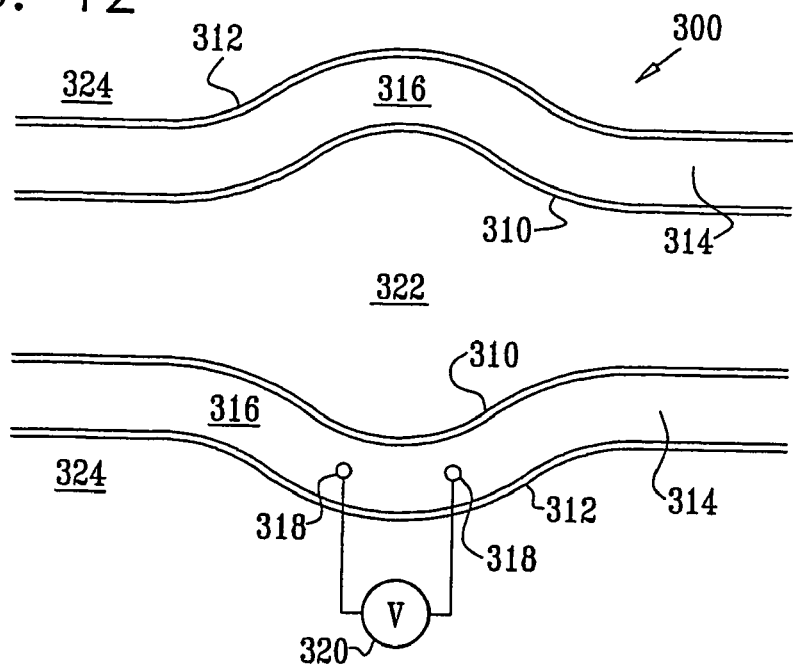
FIGS. 12 and 13 are schematic cross-sectional views of double-layered inflatable bladders, in accordance with respective embodiments of the present invention.

Reference is now made to FIG. 12, which is a schematic cross-sectional view of a double-layered inflatable bladder 300, in accordance with an embodiment of the present invention. In an embodiment, inflatable bladder 40, as described hereinabove, for example with reference to FIGS. 2A, 2B, 3A, and 3B, comprises double-layered inflatable bladder 300. Bladder 300 comprises an inner layer 310 and an outer layer 312, which define a chamber 314 therebetween. Chamber 314 comprises a substantially non-conductive biocompatible fluid 316, such as silicone oil. Chamber 314 also comprises two or more electrodes 318, which are coupled to current-sensing means 320 for sensing current flow between the electrodes. Current-sensing means 320 comprise, for example, a voltage source that applies a known small voltage between electrodes 318, and a current sensor that detects a current that flows in response to the applied voltage. Other means for detecting such current flow will be evident to those skilled in the art, having read the present application, and are within the scope of the present invention.

So long as both inner layer 310 and outer layer 312 remain completely intact, electrodes 318 are electrically isolated from one another by substantially non-conductive fluid 316. However, if either layer 310 or 312 is breached, electrically conductive biological fluid enters chamber 314, causing electrodes 318 to come into electrical contact with one another. In the case of a breach of inner layer 310, blood 322 enters chamber 314, while in the case of a breach of outer layer 312, interstitial fluid 324 enters the chamber. Current-sensing means 320 detects the electrical contact between electrodes 318.

Upon detection of such electrical contact, which is indicative of a leak in either layer 310 or 312, system 10 typically performs at least one responsive action, such as:

notifying subject 18 of the leak, such as by (a) activating an implanted vibrator, (b) sounding an alarm that is either internal or external to the body of subject 18, and/or (c)

sending a signal, either wirelessly or over wires, to an external device, such as a watch worn by subject 18, or an external monitor. Responsively to receiving such notification, subject 18 contacts a healthcare worker, and/or follows other instructions for minimizing any risk potentially associated with the leak; and/or if system 10 is performing active treatment, as defined hereinabove, ceasing to perform such active treatment.

In an embodiment of the present invention, chamber 314 comprises at least one electrode 318 (typically exactly one electrode 318), which is in electrical contact with a first terminal of current-sensing means 320. A second terminal of means 320 is in contact with extracellular fluid (i.e., blood 322 and/or interstitial fluid 324) in a vicinity of bladder 300. So long as both inner layer 310 and outer layer 312 remain completely intact, the first and second terminals are electrically isolated from one another by substantially non-conductive fluid 316, inner layer 310, and outer layer 312. However, if either layer 310 or 312 is breached, electrically conductive biological fluid enters chamber 314, causing electrode 318 to come into electrical communication with the second terminal via the extracellular fluid (which is now in electrical communication with the electrically-conductive fluid in chamber 314). Current-sensing means 320 detects the electrical contact between the first and second terminals. (Configuration not shown.)

Figure 13:
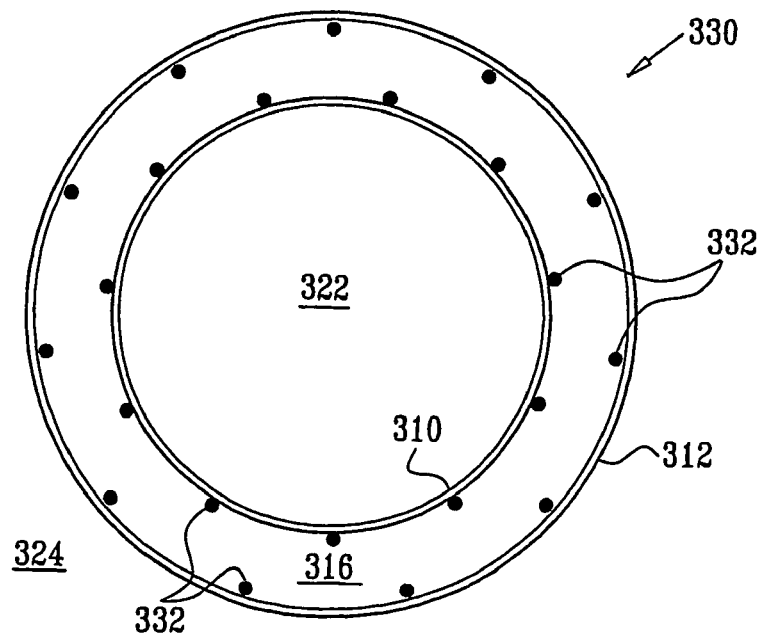

FIG. 13 is a schematic cross-sectional view of a double-layered inflatable bladder 330, in accordance with an embodiment of the present invention. Except as described below, bladder 330 is substantially the same as bladder 300, described hereinabove with reference to FIG. 12. Electrodes 318 of bladder 330 comprise two or more elongated electrodes 332, such as wires or strips of conductive coating, typically arranged longitudinally in bladder 330, in contact with substantially non-conductive fluid 316. In the configuration shown in FIG. 13, elongated electrodes 332 are coupled to inner layer 310 and outer layer 312. When elongated electrodes 332 comprise strips of conductive coating, the conductive coating is applied to inner layer 310 and/or outer layer 312, such as by painting the coating on the layers. For some applications, elongated electrodes 332 have a length of at least about 10 cm.

Each of elongated electrodes 332 is typically electrically coupled to a respective terminal of current-sensing means 320. In embodiments in which three or more elongated electrodes 332 are provided, current-sensing means 320 typically comprises a corresponding number of terminals, but may have as few as two terminals, each coupled to one or more of elongated electrodes 332. If either layer 310 or 312 is breached, electrically conductive biological fluid enters chamber 314, causing at least two of elongated electrodes 332 to come into electrical contact with one another.

Figure 14B:
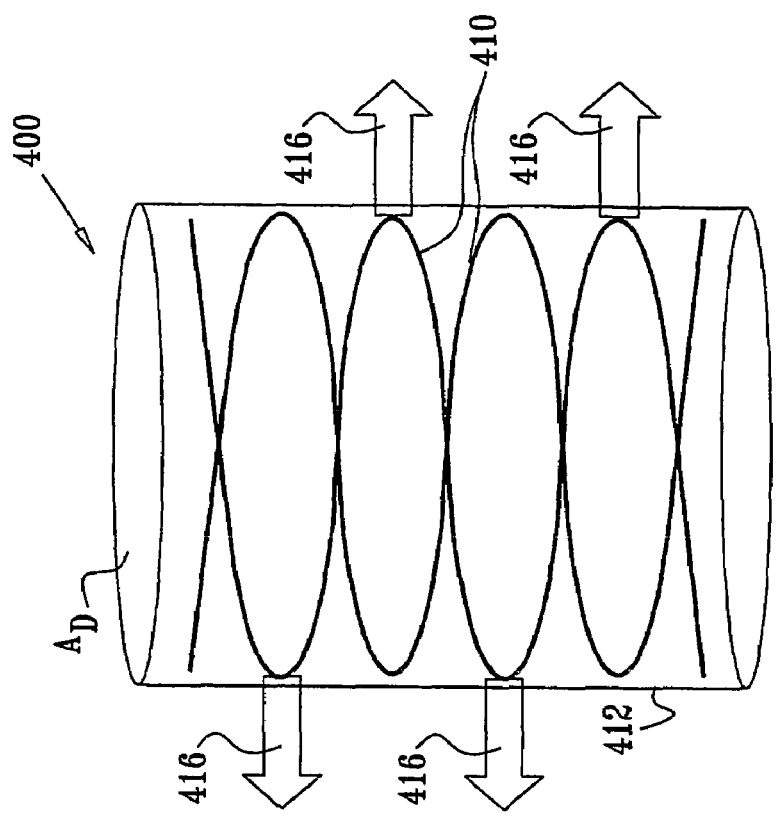
FIGS. 14A and 14B are schematic illustrations of a counterpulsation system at end-systole and end-diastole, respectively, in accordance with an embodiment of the present invention.
Figure 14A:
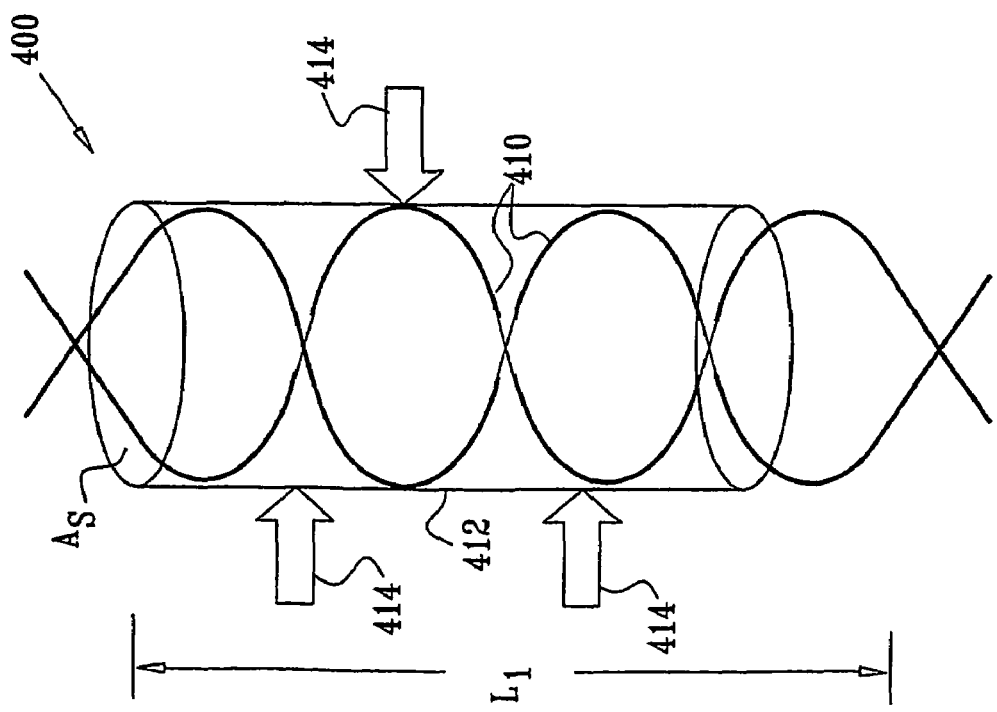

Reference is now made to FIGS. 14A and 14B, which are schematic illustrations of a counterpulsation system 400 at end-systole and end-diastole, respectively, in accordance with an embodiment of the present invention. System 400 comprises one or more springs 410, which are adapted to be inserted into an artery 412 of a subject, such as an aorta, e.g., a descending aorta, and positioned parallel to a longitudinal axis 469 of the artery. Typically, each of springs 410 is planar, i.e., flat rather than helical, and has a generally sinusoidal shape. For applications comprising more than one spring 410, the plurality of springs 410 are arranged in substantially a single plane. Optionally, springs 410 are coupled to one another at least a portion of the points at which they intersect. As discussed below, system 400 causes artery 412 to have a cross-sectional area $A_S$ at end-systole, and a smaller cross-sectional area $A_D$ of elliptical shape at end-diastole.

During systole, as shown in FIG. 14A, blood pressure within artery 412 increases, causing the cross-sectional area to increase, i.e., causing the artery to assume a more circular cross-section as the cross-sectional area approaches area $A_S$. This shape change causes the wall of the artery to move in the direction indicated by arrows 414, thereby applying force to springs 410. Springs 410 elongate relative to their shape at end-diastole (FIG. 14B), resulting at end-systole in the shape schematically shown in FIG. 14A. As springs 410 elongate, they store potential energy. As a result, a portion of the systolic blood pressure is converted to potential energy, thereby lowering systolic blood pressure relative to systolic blood pressure without treatment with system 400.

During diastole, as shown in FIG. 14B, blood pressure within artery 412 decreases, so that less blood pressure is applied to the wall of the artery. Springs 410 shorten longitudinally and expand laterally towards their neutral positions, in the direction indicated by arrows 416, applying force to the wall of the artery. This force causes the artery to assume a more elliptical cross-section as the cross-sectional area approaches $A_D$. As a result, the potential energy stored in springs 410 during systole increases blood pressure during diastole relative to diastolic blood pressure without treatment with system 400. This increased diastolic blood pressure, combined with the decreased systolic blood pressure described hereinabove with reference to FIG. 14A, provide counterpulsation treatment to the circulation of the subject.

It is noted that $A_D$ as a result of treatment is typically substantially lower than the end-diastolic cross-sectional area of the artery in the absence of treatment. Depending on the size and spring constant of each spring 410, $A_D$ may be 5-30% lower, 30-60% lower, or 60-90% lower than the end-diastolic cross-sectional area of the artery in the absence of treatment. For some applications, suitable spring parameters are chosen such that at end diastole the artery is effectively, momentarily, emptied (e.g., $A_D$ is less than 10% of the end-diastolic cross-sectional area of the artery in the absence of treatment). For some applications, springs 410 are configured to cause a ratio of (a) a major axis of artery 412 when assuming the elliptical cross-sectional shape to (b) an end-diastolic diameter of artery 412 when not assuming the elliptical cross-sectional shape to be between about 1.1 and about 1.4. Alternatively or additionally, springs 410 are configured to cause a ratio of a major axis to a minor axis of artery 412 when assuming the elliptical cross-sectional shape to be between about 1.5:1 and about 3:1.

Springs 410 are typically configured to result in a diastolic diameter of artery 412 that is between about 10% and about 40% less than a systolic diameter of the artery. This reduction in diameter typically results in diastolic cross-sectional area $A_D$ being between about 10% and about 60% less than systolic cross-sectional area $A_S$.

In an embodiment of the present invention, prior to implantation of springs 410 in a patient, the compliance of artery 412 in the patient is assessed, and appropriate springs 410 are selected responsive to the assessed compliance. For example, springs 410 having a suitable spring constant may be selected for implantation responsive to the assessed compliance. For some applications, the compliance of artery 412 is assessed via an invasive diagnostic procedure. Alternatively or additionally, the compliance is measured via a non-invasive diagnostic procedure, e.g., a blood test, an ultrasound assessment, or another test known in the art for assessing blood vessel compliance.

In an embodiment of the present invention, one or more springs 410 are positioned perpendicular to longitudinal axis 469 of the artery 412 (configuration not shown). In this embodiment, springs 410 elongate during diastole, and shorten during systole.

In an embodiment of the present invention, artery 412 includes a peripheral artery, such as a peripheral artery having a diameter of at least about 1 cm. For some applications, the counterpulsation treatment provided by system 400 provides increased diastolic blood pressure and/or perfusion to an organ of the subject supplied by the peripheral artery.

Figure 15B:
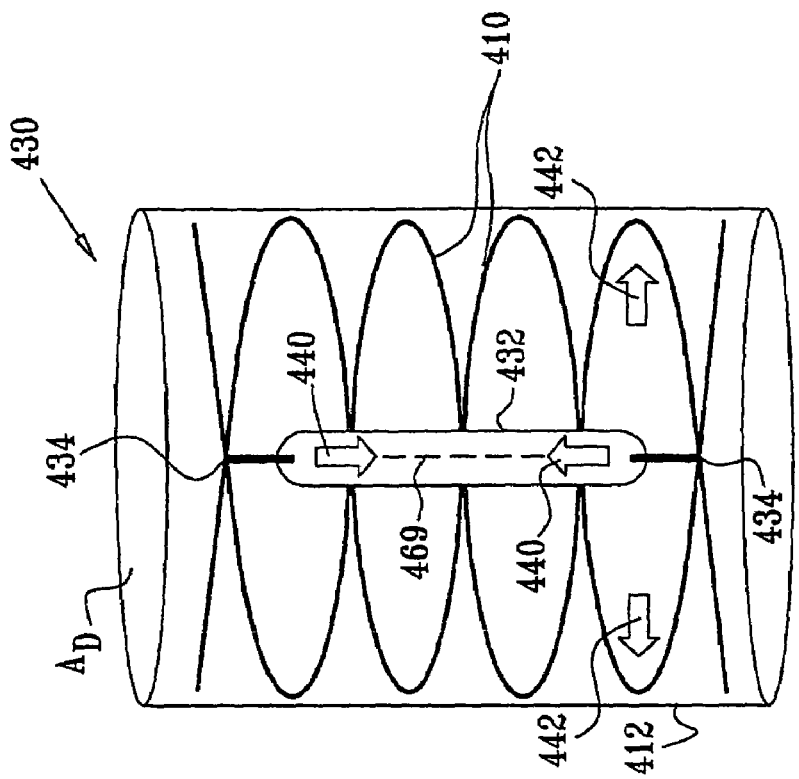
FIGS. 15A and 15B are schematic illustrations of a motorized counterpulsation system during systole and the middle of diastole, respectively, in accordance with an embodiment of the present invention.
Figure 15A:
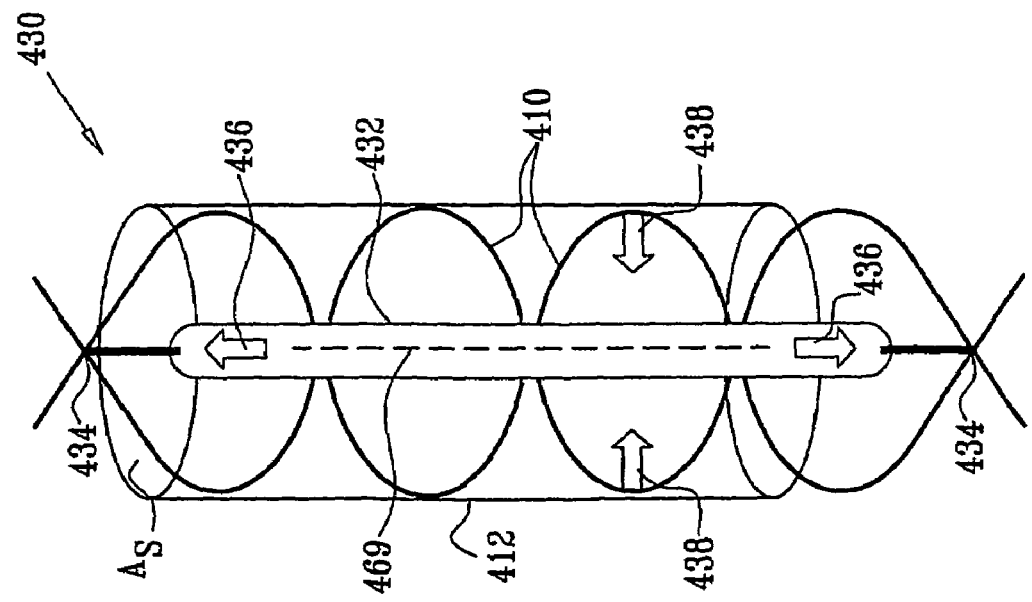

FIGS. 15A and 15B are schematic illustrations of a motorized counterpulsation system 430 during systole and the middle of diastole, respectively, in accordance with an embodiment of the present invention. Except as described below, system 430 is similar to system 400, described hereinabove with respect to FIGS. 14A and 14B. System 430 additionally comprises a motor 432, typically coupled to springs 410 at two points 434, each in a vicinity of an end of springs 410. Springs 410 typically come in contact with one another at points 434. Springs 410 of system 430 are typically configured to have lower spring constants than springs 410 of non-motorized system 400. As a result, the forces stored and applied by the springs in system 430 are less than those stored and applied by the springs in system 400. For some applications, system 430 comprises only a single spring 410.

Immediately prior to systole (e.g., at a point in time between the P-wave and R-wave of the ECG), as shown in FIG. 15A, motor 432 applies longitudinal force towards the ends of springs 410, as indicated by arrows 436. This force causes springs 410 to contract laterally, in the direction indicated by arrows 438, causing the cross-sectional area of artery 412 to increase, i.e., causing the artery to assume a more circular cross-section as the cross-sectional area approaches area $A_S$. (In this embodiment, and in the embodiments described hereinbelow with reference to FIGS. 16A, 16B, 17A, and 17B, area $A_S$ and area $A_D$ are the cross-sectional areas of artery 412 during systole and the middle of diastole, respectively.) In some cases, the resulting increased volume of artery 412 in the vicinity of system 430 lowers systolic blood pressure relative to systolic blood pressure without treatment with system 430, and lowers afterload relative to afterload without treatment with system 430. To a varying degree depending on the spring constant, the elasticity of springs 410 supports the action of motor 432, by means of the mechanism described hereinabove with respect to FIG. 14A, thereby reducing the energy consumption of the motor. For some applications, springs 410 reduce the energy consumption of motor 432 by at least about 80%. For some applications, motor 432 applies the longitudinal force during systole, such as early in systole.

During diastole, as shown in FIG. 15B, motor 432 applies longitudinal force towards the longitudinal center of springs 410, as indicated by arrows 440. This force causes springs 410 to expand laterally, in the direction indicated by arrows 442, causing the artery to assume a more elliptical cross-section as the cross-sectional area approaches $A_D$. The resulting decreased volume of artery 412 in the vicinity of system 430 increases diastolic blood pressure relative to diastolic blood pressure without treatment with system 430. To a varying degree depending on the spring constant, the elasticity of springs 410 supports the action of motor 432, by means of the mechanism described hereinabove with respect to FIG. 14B. This increased diastolic blood pressure, combined for some applications with the decreased systolic blood pressure described hereinabove with reference to FIG. 15A, provide counterpulsation treatment to the circulation of the subject.

Figure 16A:
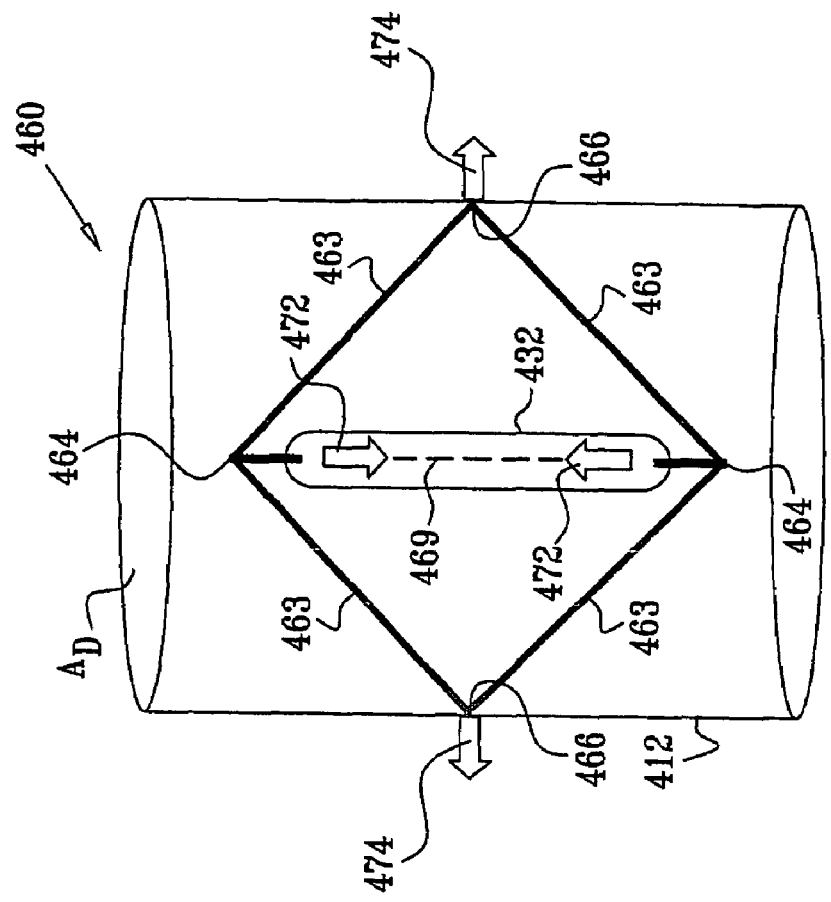
FIGS. 16A and 16B are schematic illustrations of another motorized counterpulsation system during systole and the middle of diastole, respectively, in accordance with an embodiment of the present invention.
Figure 16B:
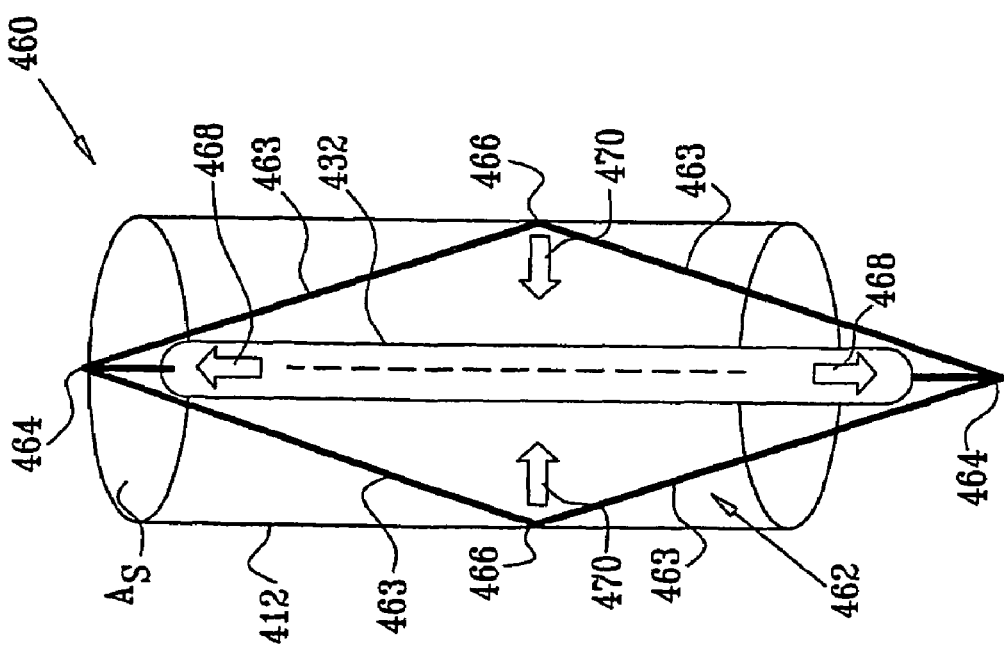

FIGS. 16A and 16B are schematic illustrations of a motorized counterpulsation system 460 during systole and the middle of diastole, respectively, in accordance with an embodiment of the present invention. System 460, rather than comprising springs 410, comprises a frame 462. Motor 432 is coupled to ends 464 of frame 462, such that the frame transforms longitudinal force applied by motor 432 into lateral movement of central side areas 466 of the frame, which are in mechanical communication with the wall of artery 412. For some applications, frame 462 is diamond-shaped, and comprises four substantially rigid articulating elongated members 463. Alternatively, frame 462 has another geometry and/or configuration that enables the frame to transform longitudinal force into lateral movement. Further alternatively, motor 432 generates lateral movement directly, and frame 462 applies force responsive thereto to the wall of artery 412. For some applications, frame 462 comprises a plurality of segments, e.g., linked articulating diamond-shaped segments, typically arranged longitudinally (configuration not shown).

Immediately prior to systole (e.g., at a point in time between the P-wave and R-wave of the ECG), as shown in FIG. 16A, motor 432 applies longitudinal force towards ends 464, as indicated by arrows 468, longitudinally stretching frame 462. As a result, central side areas 466 of frame 462 move towards longitudinal axis 469 of artery 412, as indicated by arrows 470, causing the cross-sectional area of artery 412 to increase, i.e., causing the artery to assume a more circular cross-section as the cross-sectional area approaches area $A_S$. The resulting increased volume of artery 412 in the vicinity of system 460 lowers systolic blood pressure, for some applications to a value lower than systolic blood pressure without treatment with system 460. For some applications, motor 432 applies the longitudinal force during systole, such as early in systole.

During diastole, as shown in FIG. 16B, motor 432 applies longitudinal force towards the center of frame 462, as indicated by arrows 472, longitudinally compressing frame 462. As a result, central side areas 466 of frame 462 move away from longitudinal axis 469 of artery 412, as indicated by arrows 474, causing the artery to assume a more elliptical cross-section as the cross-sectional area approaches $A_D$. The resulting decreased volume of artery 412 in the vicinity of system 460 increases diastolic blood pressure relative to diastolic blood pressure without treatment with system 460. This increased diastolic blood pressure, typically combined with the decreased systolic blood pressure described hereinabove with reference to FIG. 16A, provide counterpulsation treatment to the circulation of the subject.

FIGS. 17A and 17B are schematic illustrations of a motorized counterpulsation system 490 during systole and the middle of diastole, respectively, in accordance with an embodiment of the present invention. System 490 comprises (a) motor 432 and springs 410, as described hereinabove with reference to FIGS. 15A and 15B, and (b) frame 462, as described hereinabove with reference to FIGS. 16A and 16B. Motor 432 is thus coupled to both springs 410 and frame 462. The elasticity of springs 410 supports the action of motor 432, thereby reducing the energy consumption of the motor. For some applications, springs 410 reduce the energy consumption of motor 432 by at least about 80%.

Immediately prior to systole (e.g., at a point in time between the P-wave and R-wave of the ECG), as shown in FIG. 17A, motor 432 applies longitudinal force towards ends 464, as indicated by arrows 492. This force (a) causes springs 410 to contract laterally, in the direction indicated by arrows 438, and (b) longitudinally stretches frame 462, moving central side areas 466 of frame 462 towards longitudinal axis 469 of artery 412, as indicated by arrows 470. This combined motion of springs 410 and frame 462 causes the cross-sectional area of artery 412 to increase, i.e., causes the artery to assume a more circular cross-section as the cross-sectional area approaches area $A_S$. The resulting increased volume of artery 412 in the vicinity of system 490 lowers systolic blood pressure, for some applications to a value lower than systolic blood pressure without treatment with system 490. For some applications, motor 432 applies the longitudinal force during systole, such as early in systole.

During diastole, as shown in FIG. 17B, motor 432 applies longitudinal force towards the center of frame 462, as indicated by arrows 494. This force (a) causes springs 410 to expand laterally, in the direction indicated by arrows 442, and (b) longitudinally compresses frame 462, moving central side areas 466 of frame 462 away from longitudinal axis 469 of artery 412, as indicated by arrows 474. This combined motion of springs 410 and frame 462 causes the artery to assume a more elliptical cross-section as the cross-sectional area approaches $A_D$. The resulting decreased volume of artery 412 in the vicinity of system 490 increases diastolic blood pressure relative to diastolic blood pressure without treatment with system 490. This increased diastolic blood pressure, typically combined with the decreased systolic blood pressure described hereinabove with reference to FIG. 17A, provide counterpulsation treatment to the circulation of the subject.

For some applications, springs 410 are configured not to come in contact with the wall of artery 412. In these applications, springs 410 serve only to support the action of motor 432.

In an embodiment of the present invention, system 460 or system 490 comprises motor 432, but no frame (configuration not shown). In this embodiment, motor 432 applies force to the wall of artery 412. For example, the motor may be positioned in artery 412 perpendicular to longitudinal axis 469 of the artery. For some applications, the system further comprises at least one spring, arranged so as to support the operation of the motor. For example, the spring may be arranged parallel to the motor, e.g., surrounding the motor.

In an embodiment of the present invention, system 430, system 460, or system 490 comprises control circuitry implementing at least a portion of the features of control circuitry 70, described hereinabove with reference to FIG. 4. For example, system 430, system 460, or system 490 may implement at least a portion of the cardiac cycle synchronization techniques of control circuitry 70.

Figure 18A:
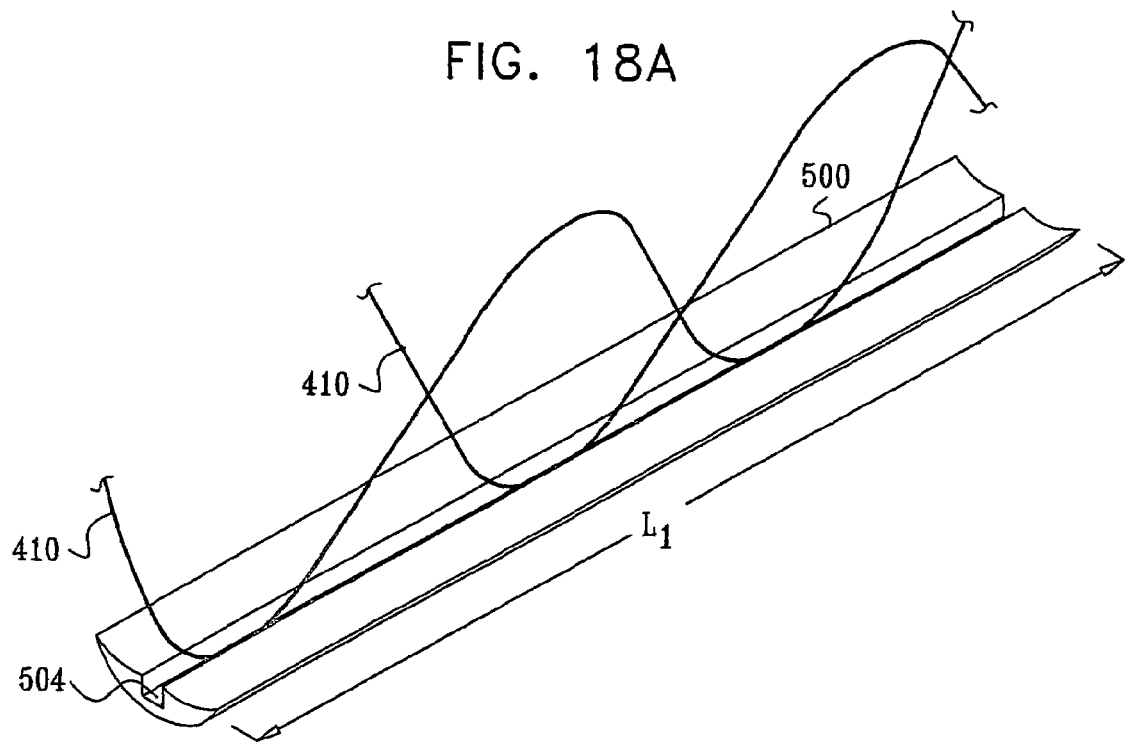
FIGS. 18A and 18B are a pictorial view and a schematic cross-sectional view, respectively, of a protective element and a set of protective elements, respectively, in accordance with an embodiment of the present invention.
Figure 18B:
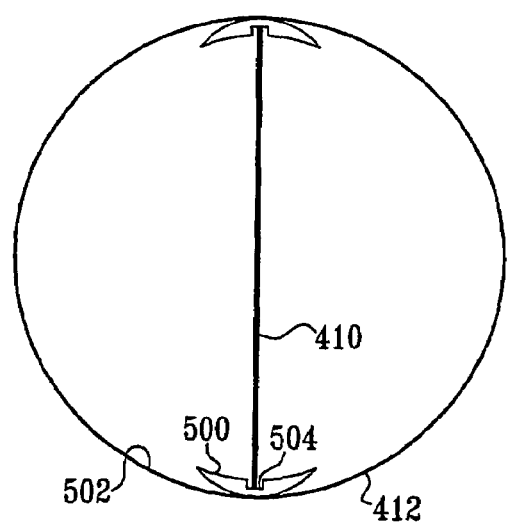

FIGS. 18A and 18B are a pictorial view and a schematic cross-sectional view, respectively, of a protective element 500 and a set of protective elements 500, respectively, in accordance with an embodiment of the present invention. Elements 500 are adapted to provide a protective interface between a wall 502 of artery 412 and one or more springs 410, as described hereinabove with reference to FIGS. 14A, 14B, 15A, 15B, 17A, and 17B. This protective interface prevents rubbing of springs 410 against wall 502 as springs 410 elongate and shorten during the cardiac cycle. (For clarity of illustration only a single element 500 is shown in FIG. 18A; in actual use, a second element 500 protects wall 502 on its opposite side, as seen in FIG. 18B.) For applications in which springs 410 are positioned parallel to longitudinal axis 469 of artery 412, element 500 typically is shaped to define a groove 504, in which springs 410 slide longitudinally as the springs elongate and shorten. Element 500 is typically of a length sufficient to accommodate springs 410 in their most elongated positions, e.g., a length of approximately length $L_1$ (shown both in FIG. 18A and in FIG. 14A). For some applications, length $L_1$ is between about 5 and about 30 cm.

Figure 19A:
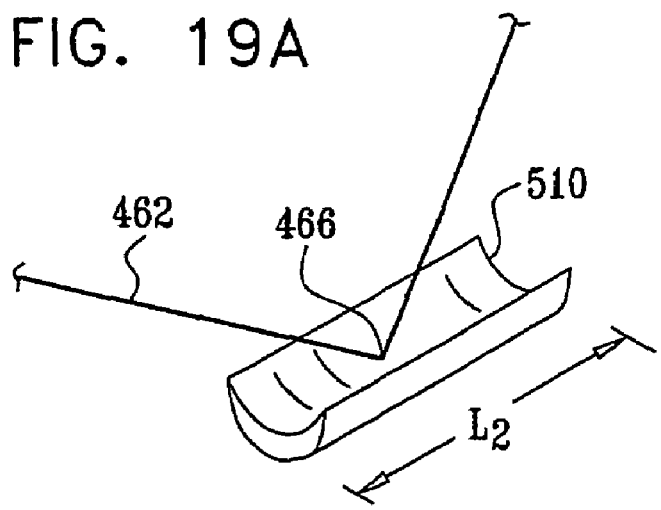
FIGS. 19A and 19B are a pictorial view and a schematic cross-sectional view, respectively, of another protective element and a set of protective elements, respectively, in accordance with an embodiment of the present invention.
Figure 19B:
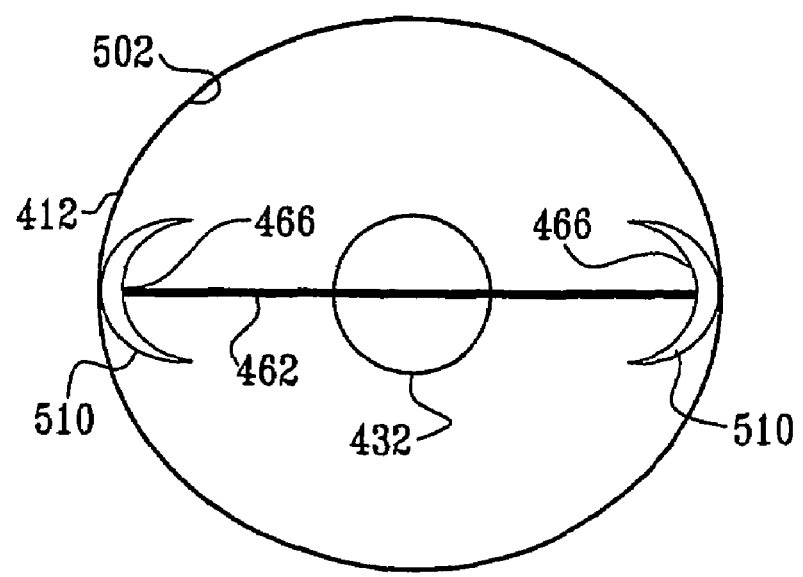

FIGS. 19A and 19B are a pictorial view and a schematic cross-sectional view, respectively, of a protective element 510 and a set of protective elements 510, respectively, in accordance with an embodiment of the present invention. Similar to elements 500, elements 510 are adapted to provide a protective interface between wall 502 of artery 412 and central side areas 466 of frame 462, as described hereinabove with reference to FIGS. 16A, 16B, 17A, and 17B. This protective interface prevents any damage that might otherwise be caused by frame 462 to wall 502. (For clarity of illustration only a single element 510 is shown in FIG. 19A; in actual use, a second element 510 protects wall 502 on its opposite side, as shown in FIG. 19B.) Element 510 typically has a length $L_2$ of between about 5 and about 30 cm.

It is to be understood that substantially any suitable couplings known in the art may be used to attach frame 462 to central side areas 466.

In an embodiment of the present invention, motor 432, as described hereinabove with reference to FIGS. 15A, 15B, 16A, 16B, 17A, and 17B, comprises an artificial muscle, as described in the Background of the Invention hereinabove. Alternatively, other suitable motor mechanisms known in the art may be used. For example, motor 432 may comprise a linear motor.

For some applications, systems 400, 430, 460, and 490 are adapted to be inserted into artery 412, e.g., an aorta, by a transcatheter approach, e.g., via a femoral artery of the subject.

Figure 20:
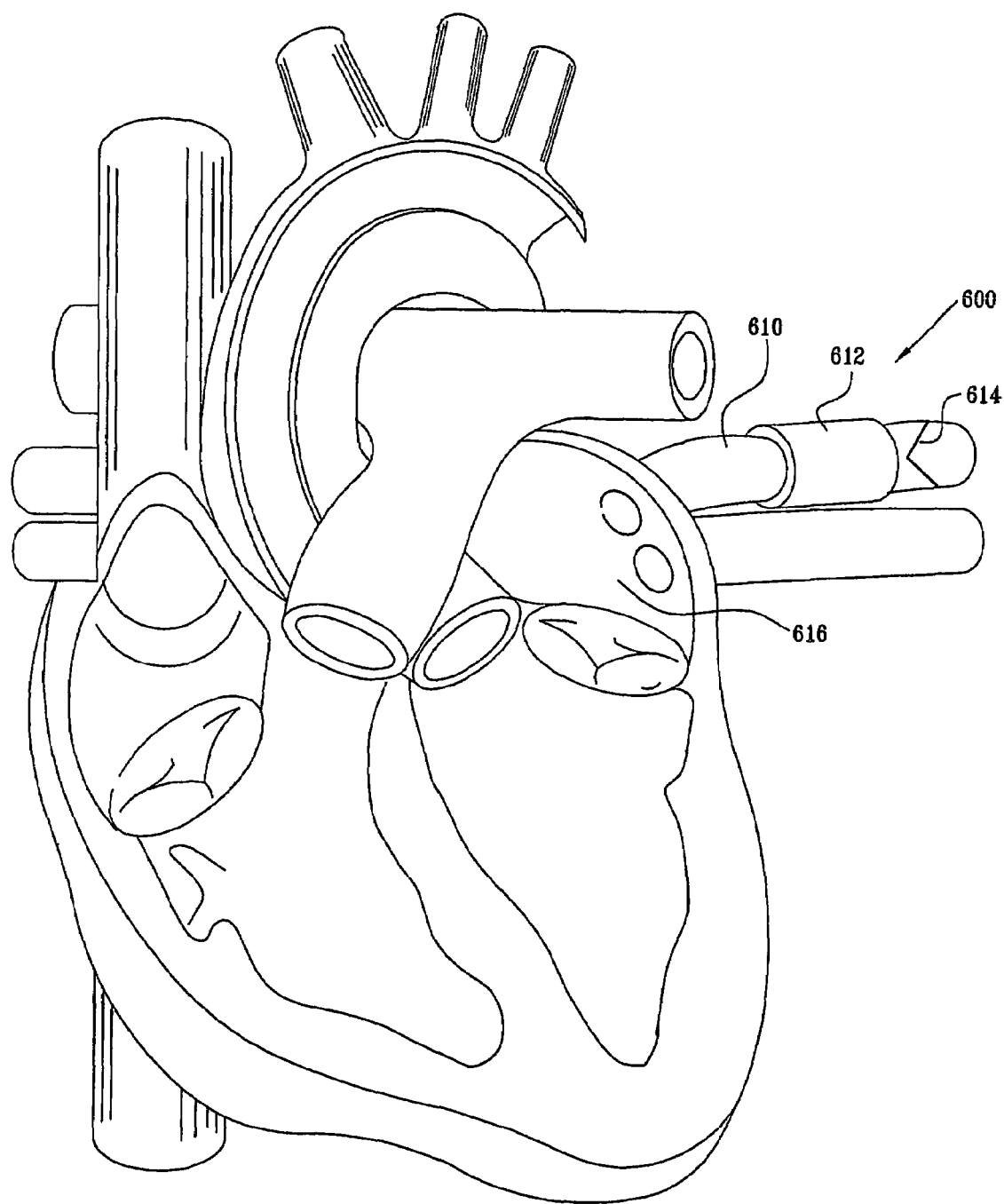
FIG. 20 is a schematic illustration of a counterpulsation system coupled to a pulmonary vein of a subject, in accordance with an embodiment of the present invention.

Reference is now made to FIG. 20, which is a schematic illustration of a counterpulsation system 600 coupled to a pulmonary vein 610 of a subject, in accordance with an embodiment of the present invention. System 600 is implanted in pulmonary vein 610 (a) in series, as shown in FIG. 20, (b) in parallel, similar to the configuration shown in FIG. 1B, or (c) to a single opening in pulmonary vein 610, similar to the configuration shown in FIG. 1E. System 600 comprises a counterpulsation device 612, such as any of the counterpulsation devices described hereinabove, or any other counterpulsation device known in the art, e.g., one of the counterpulsation devices described in the Background of the Invention. System 600 further comprises a unidirectional valve 614, which is either integrated into counterpulsation device 612, or implanted elsewhere in pulmonary vein 610. Valve 614 substantially prevents backflow of blood from pulmonary vein 610 to the lungs. System 600 is adapted to treat diastolic heart failure by increasing the flow of blood from one or both of the lungs to a left atrium 616. For some applications, a plurality of counterpulsation systems 600 are coupled to a plurality of pulmonary veins of the subject.

In an embodiment of the present invention, system 10 is used in combination with one or more of the following:

a pacemaker, e.g., a bi-ventricular pacemaker, which serves to regulate heart activity to support the healing process. In combination with the techniques described herein for lowering systolic blood pressure, pacemakers can effectively be used to increase heart rate and therefore cardiac output, without a concomitant increase systolic blood pressure;

stimulation of the vagus nerve so as to decrease heart rate, for example by using techniques described in U.S. Pat. No. 6,473,644 to Terry, Jr. et al., and/or U.S. Pat. No. 5,203,326 to Collins, which are incorporated herein by reference;

a medication. For example, the techniques described herein may be used in order to allow a decrease in a dosage of the medication (e.g., beta-blockers, which are often administered to reduce blood pressure);

a VAD;

cell and/or gene therapy, which, among other applications, attempt to repair and augment diseased cardiac muscles. Because these forms of therapy are generally sensitive to heart stress, treatment using the techniques described herein generally enables these techniques to be more successful and/or effective. For some applications, techniques described herein are used in conjunction with cell therapy, for example using techniques described in the above-cited U.S. Pat. No. 5,130,141 to Law et al. and/or PCT Publication WO 02/28470 to Law. Alternatively or additionally, techniques described herein are used in conjunction with gene therapy, for example using techniques described in the above-cited U.S. Pat. No. 6,297,220 to Leiden et al., U.S. Pat. No. 6,100,242 to Hammond et al., and/or U.S. Pat. No. 6,306,830 to Hammond et al.;

defibrillation, such as performed with a defibrillator;

nerve fiber stimulation techniques described in the above-referenced US Patent Application 2003/0045909 to Gross et al.;

heart rate reduction techniques described in the above-referenced PCT Publication WO 03/099377 to Ayal et al.; and/or a cardiac assist device, such as a sheath, cuff, or cup that surrounds at least a portion of the heart and applies a mechanical force that squeezes the heart in order to pump blood therethrough. For example, the techniques described herein may be used in combination with techniques that are described in one or more of the following patents, all of which are incorporated herein by reference: U.S. Pat. No. 4,048,990 to Goetz, U.S. Pat. No. 4,192,293 to Asrican, U.S. Pat. No. 4,536,893 to Parravicini, U.S. Pat. No. 5,119,804 to Anstadt, U.S. Pat. No. 6,206,820 to Kazi et al., and U.S. Pat. No. 6,254,525 to Reinhardt et al.

Although the counterpulsation systems described herein have been described herein as being coupled to an artery of the systemic circulation (except with reference to FIG. 20), in some embodiments of the present invention, the counterpulsation systems are coupled to a pulmonary artery, and the techniques described herein are applied, mutatis mutandis.

It is to be understood that whereas some embodiments of the present invention are described hereinabove with respect to controlling blood flow by use of a valve, the scope of the present invention includes the use of valve means having substantially no moving parts, but which bias flow in a predetermined direction by virtue of the shape of the valve means.

In the context of the present patent application and in the claims, the phrase "immediately prior to systole," and variants thereof, is to be understood as meaning the period starting at 100 ms before an ECG P-wave, and extending through the onset of systole.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    an inflatable bladder, configured to be coupled to a blood vessel of a subject carrying oxygenated blood, such that an interior of the bladder is in fluid communication with the blood;
    a piston that comes in contact with an external surface of the bladder;
    a motor, configured to synchronize contraction and expansion of the bladder with a cardiac cycle of the subject by applying a motor force to the piston; and
    a spring, configured to apply a spring force to the piston,
    wherein the bladder is shaped so as to define inflow and outflow conduits,
    wherein the bladder is configured such that the interior of the bladder is in the fluid communication with the blood via the inflow and outflow conduits,
    wherein the piston comes in contact with a central portion of the bladder, and
    wherein the apparatus is configured such that upon the expansion of the bladder, a cross-sectional area of the central portion of the bladder is greater than a cross-sectional area of the inflow conduit.

2. The apparatus according to claim 1, wherein the bladder is configured to be coupled to the blood vessel by coupling the inflow conduit to a first site of the blood vessel, and the outflow conduit to a second site of the blood vessel, such that the first site and second site are in fluid communication with one another only via the bladder.

3. The apparatus according to claim 1, comprising a case, configured to prevent the bladder from expanding in a certain direction beyond a predetermined extent.

4. The apparatus according to claim 1, comprising a locking mechanism, configured to lock the piston in place for a portion of the cardiac cycle.

5. The apparatus according to claim 1, wherein the bladder is shaped so as to define a single anastomosis site, and is configured to be coupled to the blood vessel by anastomosis through a single opening in a wall of the blood vessel.

6. The apparatus according to claim 1, wherein the motor comprises a linear motor.

7. The apparatus according to claim 1, wherein the spring is configured to reduce an energy consumption of the motor by at least about 80% compared to the energy consumption in the absence of the spring.

8. The apparatus according to claim 1, wherein the apparatus is configured such that, in the event of a failure of the motor, the apparatus provides passive counterpulsation treatment to the subject.

9. The apparatus according to claim 1, wherein the bladder is configured to be coupled to the blood vessel by coupling the inflow conduit to a first site of the blood vessel, and the outflow conduit to a second site of the blood vessel, such that the first site and the second site are in fluid communication with one another via the blood vessel and via the bladder.

10. The apparatus according to claim 9, wherein one of the inflow and outflow conduits comprises a constriction element, configured to cause asymmetric blood flow through the bladder.

11. The apparatus according to claim 1, comprising a sensor, configured to sense a physiological parameter of the subject and to generate a sensor signal responsive thereto, wherein the motor is configured to synchronize the contraction and the expansion of the bladder responsive to the sensor signal.

12. The apparatus according to claim 11, wherein the physiological parameter includes a blood pressure of the subject, and wherein the sensor is configured to sense the blood pressure and to generate the sensor signal responsive thereto.

13. The apparatus according to claim 11, wherein the physiological parameter includes an electrocardiographic parameter of the subject, and wherein the sensor is configured to sense the electrocardiographic parameter and to generate the sensor signal responsive thereto.

14. The apparatus according to claim 13, wherein the motor is configured to expand the bladder immediately prior to or during systole.

15. The apparatus according to claim 13, wherein the motor is configured to contract the bladder at a point in time during or soon after a T-wave of the ECG.

16. The apparatus according to claim 1, configured such that throughout the cardiac cycle, an apparatus-induced blood-containing volume of the blood vessel and the bladder in a vicinity of the apparatus is greater than or equal to an apparatus-absent blood-containing volume of the blood vessel in the vicinity in the absence of the apparatus.

17. The apparatus according to claim 1, configured such that upon the expansion of the bladder, an apparatus-induced blood-containing volume of the blood vessel and the bladder in a vicinity of the apparatus is greater than an apparatus-absent blood-containing volume of the blood vessel in the vicinity in the absence of the apparatus.

18. Apparatus comprising:
an inflatable bladder, comprising:
an inner layer and an outer layer, which define a chamber therebetween, the inner layer defining an interior of the bladder;
a biocompatible substantially non-conductive fluid, contained within the chamber;
two or more electrodes, in contact with the substantially non-conductive fluid; and
a current sensing unit, coupled to the electrodes and configured to sense current flow between at least two of the electrodes,
wherein the bladder is configured to be implanted in a subject such that the interior of the bladder is in fluid communication with blood of a blood vessel of the subject.

19. The apparatus according to claim 18, wherein at least one of the electrodes comprises a wire having a length of at least 10 cm.

20. The apparatus according to claim 18, wherein at least one of the electrodes comprises a conductive coating applied to a surface selected from: the inner layer and the outer layer.

21. The apparatus according to claim 18, wherein the substantially non-conductive fluid comprises silicone oil.

22. The apparatus according to claim 18, comprising a control unit, adapted to:
receive, from the current sensing unit, a signal indicative of a level of the sensed current flow, and
generate a notification signal when the level of the current flow crosses a threshold value.

23. The apparatus according to claim 18, wherein the current sensing unit comprises:

a voltage source, adapted to apply a known small voltage between the electrodes; and
a current sensor, adapted to detect a current that flows in response to the applied voltage.

24. Apparatus comprising:
an inflatable bladder, configured to be coupled to a blood vessel of a subject carrying oxygenated blood, such that an interior of the bladder is in fluid communication with the blood;
a piston that comes in contact with an external surface of the bladder;
a motor, configured to synchronize contraction and expansion of the bladder with a cardiac cycle of the subject by applying a motor force to the piston; and
a spring, configured to apply a spring force to the piston,
wherein the bladder is shaped so as to define inflow and outflow conduits,
wherein the bladder is configured such that the interior of the bladder is in the fluid communication with the blood via the inflow and outflow conduits,
wherein the piston comes in contact with a central portion of the bladder, and
wherein the apparatus is configured such that throughout the cardiac cycle, a cross-sectional area of the central portion of the bladder is greater than or equal to a cross-sectional area of the inflow conduit.

25. The apparatus according to claim 24, comprising a case, configured to prevent the bladder from expanding in a certain direction beyond a predetermined extent.

26. The apparatus according to claim 24, wherein the apparatus is configured such that, in the event of a failure of the motor, the apparatus provides passive counterpulsation treatment to the subject.

27. The apparatus according to claim 24, comprising a sensor, configured to sense a physiological parameter of the subject and to generate a sensor signal responsive thereto, wherein the motor is configured to synchronize the contraction and the expansion of the bladder responsive to the sensor signal.

28. The apparatus according to claim 24, configured such that throughout the cardiac cycle, an apparatus-induced blood-containing volume of the blood vessel and the bladder in a vicinity of the apparatus is greater than or equal to an apparatus-absent blood-containing volume of the blood vessel in the vicinity in the absence of the apparatus.

29. The apparatus according to claim 24, configured such that upon the expansion of the bladder, an apparatus-induced blood-containing volume of the blood vessel and the bladder in a vicinity of the apparatus is greater than an apparatus-absent blood-containing volume of the blood vessel in the vicinity in the absence of the apparatus.

30. The apparatus according to claim 24, wherein the bladder is shaped so as to define a single anastomosis site, and is configured to be coupled to the blood vessel by anastomosis through a single opening in a wall of the blood vessel.

* * * * *